US010767221B2

(12) United States Patent
Gloeckner et al.

(10) Patent No.: US 10,767,221 B2
(45) Date of Patent: Sep. 8, 2020

(54) ENZYME-LINKED NUCLEOTIDES

(71) Applicant: ILLUMINA, INC., San Diego, CA (US)

(72) Inventors: Christian Gloeckner, Bonn (DE); Matthew William Kellinger, San Diego, CA (US); Lea Pickering, Caxton (GB)

(73) Assignee: Illumina, Inc., San Diego, CA (US)

( * ) Notice: Subject to any disclaimer, the term of this patent is extended or adjusted under 35 U.S.C. 154(b) by 293 days.

(21) Appl. No.: 14/776,551

(22) PCT Filed: Mar. 15, 2013

(86) PCT No.: PCT/US2013/032165
§ 371 (c)(1),
(2) Date: Sep. 14, 2015

(87) PCT Pub. No.: WO2014/142981
PCT Pub. Date: Sep. 18, 2014

(65) Prior Publication Data
US 2016/0032379 A1 Feb. 4, 2016

(51) Int. Cl.
*C12Q 1/6874* (2018.01)
*C12N 9/12* (2006.01)
*C12Q 1/6869* (2018.01)
*A61K 47/64* (2017.01)
*A61K 47/59* (2017.01)
*C12N 9/96* (2006.01)

(52) U.S. Cl.
CPC ............ *C12Q 1/6874* (2013.01); *A61K 47/59* (2017.08); *A61K 47/64* (2017.08); *C12N 9/1241* (2013.01); *C12N 9/1252* (2013.01); *C12N 9/1276* (2013.01); *C12N 9/96* (2013.01); *C12Q 1/6869* (2013.01); *C12Y 207/07007* (2013.01)

(58) Field of Classification Search
CPC ........ C12Q 2521/101; C12Q 2527/113; C12Q 2525/197; C12Q 1/6889; C12Q 1/6874; C12Q 2525/101; C12Q 1/6869; C12N 9/1241; C12N 9/1252; C12N 9/1276; C12N 9/96; C12Y 207/070007
See application file for complete search history.

(56) References Cited

U.S. PATENT DOCUMENTS

2002/0039738 A1* 4/2002 Williams ............... C07H 19/10
435/6.12
2008/0299565 A1* 12/2008 Schneider ............ C12Q 1/6818
435/6.14

FOREIGN PATENT DOCUMENTS

WO 2004/074503 9/2004
WO 2007/070542 6/2007

OTHER PUBLICATIONS

Rothwell, P.J. et al., Adv. Protein Chem., vol. 71, pp. 401-440 (2005).*

(Continued)

*Primary Examiner* — Teresa E Strzelecka
(74) *Attorney, Agent, or Firm* — Gavrilovich, Dodd & Lindsey LLP

(57) ABSTRACT

Presented herein are polymerase-linked nucleotides for improved distinguishing nucleotide sequences for different nucleic acid molecules. Also presented are methods and systems using the polymerase-linked nucleotides for improved distinguishing nucleotide sequences for different nucleic acid molecules.

8 Claims, 16 Drawing Sheets
Specification includes a Sequence Listing.

(56) References Cited

OTHER PUBLICATIONS

Loh, E. et al., J. Biol. Chem., vol. 282, pp. 12201-12209 (2007).*
Cozens, C. et al., PNAS, vol. 109, pp. 8067-8072 and supporting information pp. 1-10 (2012).*
Cramer, P. et al., Ann. Rev. Biophys., vol. 37, pp. 337-352 (2008).*

* cited by examiner

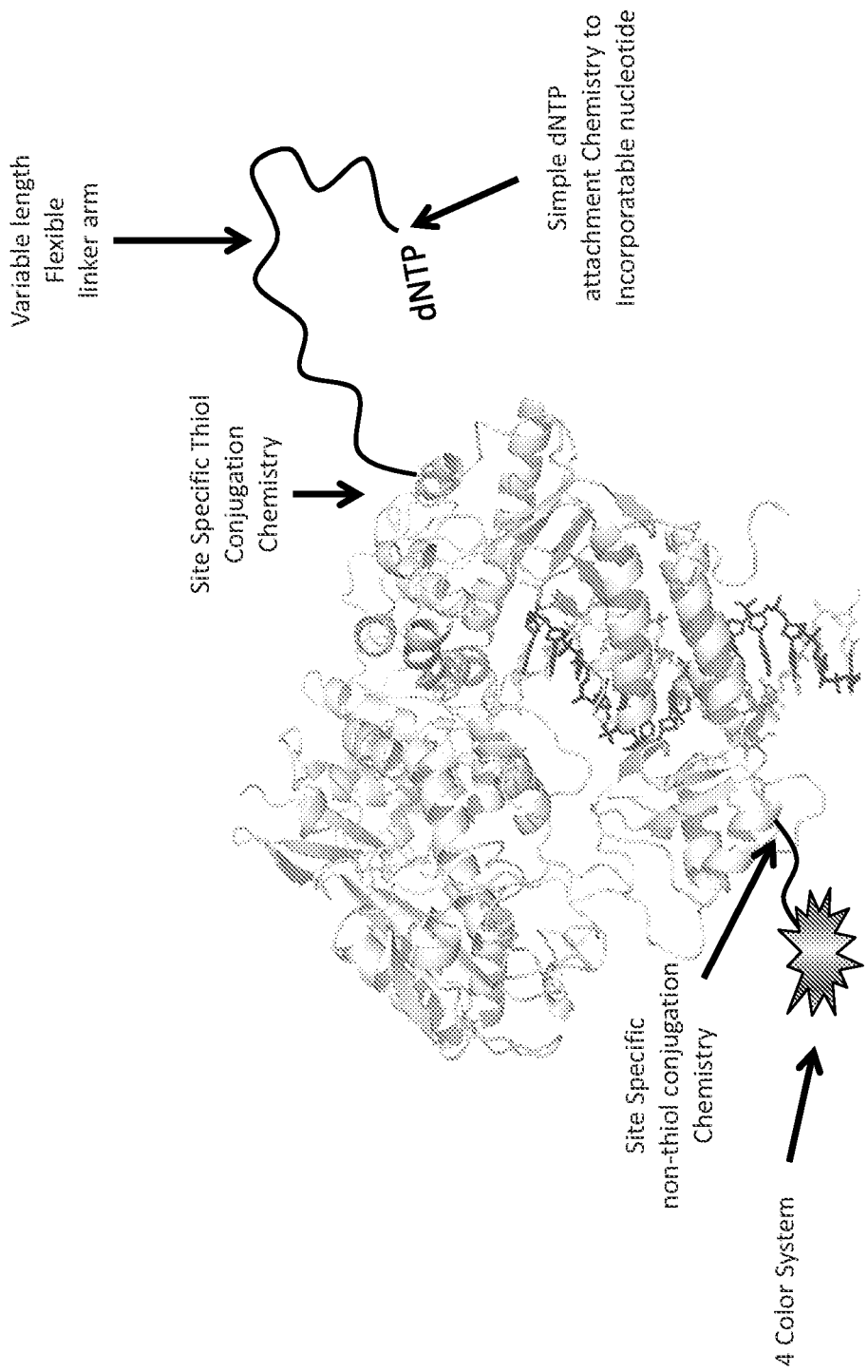

| Enzyme | Incorporation of (MeO)C-sp-BPoA | Incorporation of (MeO)C-sp-BPoA |
|---|---|---|
| BSU | ✓ | ✓ |
| Pol β | ✓ | ✓ |
| Klenow | ✓ | ✓ |
| Pol 217 | ✓ | ✓ |
| iPEG Pol 420 | ✓ | ✓ |
| iPEG Pol 812 | ✓ | ✓ |

FIG. 4C

ENZYME-LINKED NUCLEOTIDES

BACKGROUND

This disclosure relates generally to detection and characterization of nucleic acids. More specifically this disclosure relates to determining the sequences of nucleic acids.

One's genome provides a blue print for predicting many inherent predispositions such as one's likes and dislikes, talents, susceptibility to disease and responsiveness to therapeutic drugs. The human genome contains a sequence of over 3 billion nucleotides and it is the differences in just a fraction of those nucleotides that determines unique characteristics of an individual. The research community is making impressive strides in unraveling the link between genomic sequence and the living structures they encode. However, a more complete understanding will require that tens-of-thousands or millions of genomes be sequenced. Then scientists will be able to correlate the complexities of the genetic code with the variety of human characteristics. Furthermore, beyond the research effort, the costs must come down in order to usher in the day when each person will have a copy of their own personal genome so that they can sit down with their doctor to determine appropriate choices for a healthy lifestyle or a proper course of treatment.

Several commercial sequencing platforms are available, and although they provide an accurate tool for sequencing on the scale of entire genomes, they are still prohibitively expensive for wide deployment across large populations of individuals. What is needed is a reduction in the cost of sequencing that drives large genetic correlation studies carried out by research scientists and that makes sequencing accessible in hospitals and clinics to facilitate the informed treatment of individual patients making life changing decisions. The inventions set forth herein satisfy this need and provide other advantages as well.

BRIEF SUMMARY

The present disclosure provides a polymerase-linked nucleotide comprising a nucleotide covalently attached to a catalytically active polymerase enzyme by a flexible linker. In a certain embodiment, the linker attachment to the nucleotide allows the nucleotide to bind noncovalently at the active site of the polymerase. In a certain embodiment, the linker attachment to the nucleotide allows the polymerase to incorporate the nucleotide into the 3' end of a polynucleotide. In a certain embodiment, the polymerase comprises a detectable label, such as, for example a fluorophore.

The present disclosure also provides a modified polymerase comprising a pyrophosphate moiety at the terminal end of a flexible linker, the flexible linker covalently attached to a catalytically active polymerase, the composition being formed by the incorporation of a nucleotide into the 3' end of a polynucleotide by the polymerase. In a certain embodiment, the linker attachment to the nucleotide allows the nucleotide to bind noncovalently at the active site of the polymerase. In a certain embodiment, the linker attachment to the nucleotide allows the polymerase to incorporate the nucleotide into the 3' end of a polynucleotide.

The present disclosure also provides a method of distinguishing nucleotide sequences for different nucleic acid molecules, comprising (a) providing a plurality of different nucleic acid molecules, wherein the different nucleic acid molecules are attached to a surface in the form of an array of nucleic acid features; (b) adding a plurality of polymerase-linked nucleotides to the nucleic acid features, (c) monitoring binding of the polymerase molecules to the nucleic acid features, thereby determining dwell time of the polymerase molecules at the nucleic acid features; and (d) identifying nucleic acid features of the array that correctly incorporate the nucleotide molecules based on the dwell time of the polymerase molecules at the nucleic acid features, thereby distinguishing the nucleotide sequences for the different nucleic acid molecules. In certain embodiments, (b) comprises monitoring a detectable signal indicative of the binding of the polymerase molecules to the nucleic acid features and catalysis of nucleotide incorporation into the polynucleotide feature. In certain embodiments, (c) comprises identifying the nucleic acid features of the array that correctly incorporate the nucleotide molecules based on detectable signal of the polymerase molecules at the nucleic acid features, whereby the dwell time determines nucleotide molecules that are correctly incorporated into the nucleic acid features, thereby distinguishing the nucleotide sequences for the different nucleic acid molecules. In certain embodiments, (b) comprises simultaneously adding a plurality nucleotide species that base-pair with four different nucleotide species in the polynucleotide features. In certain embodiments, each of the nucleotide species is distinguished from the other nucleotide species in the plurality of species by a distinct detectable label.

The present disclosure also provides a system for distinguishing nucleotide sequences for different nucleic acid molecules, the system comprising (a) an array comprising nucleic acid features having different nucleotide sequences; (b) a fluidic apparatus configured to deliver sequencing reagents to the array, wherein the sequencing reagents comprise polymerase-linked nucleotide comprising a nucleotide covalently attached to a catalytically active polymerase enzyme by a flexible linker; (c) a detection apparatus configured to measure binding events from the array at a resolution that distinguishes individual nucleic acid features of the array; and (d) a control module comprising instructions for (i) adding the sequencing reagents to the nucleic acid features, (ii) obtaining measurements of binding of the polymerase molecules to the nucleic acid features; and (e) an analysis module comprising instructions for (i) processing the measurements of binding of the polymerase molecules to the nucleic acid features, thereby determining dwell time of the polymerase molecules at the nucleic acid features; and (ii) identifying nucleic acid features of the array that correctly incorporate the nucleotide molecules based on the dwell time of the polymerase molecules at the nucleic acid features, thereby distinguishing the nucleotide sequences for the different nucleic acid molecules. In certain embodiments, (d)(ii) comprises monitoring a detectable signal indicative of the binding of the polymerase molecules to the nucleic acid features and catalysis of nucleotide incorporation into the polynucleotide feature. In certain embodiments, (e)(ii) comprises identifying the nucleic acid features of the array that correctly incorporate the nucleotide molecules based on detectable signal of the polymerase molecules at the nucleic acid features, whereby the dwell time determines nucleotide molecules that are correctly incorporated into the nucleic acid features, thereby distinguishing the nucleotide sequences for the different nucleic acid molecules. In certain embodiments, (d)(ii) comprises monitoring a detectable signal indicative of the binding of the polymerase molecules to the nucleic acid features and catalysis of nucleotide incorporation into the polynucleotide feature. In certain embodiments, the detectable label comprises a detectable label attached to the polymerase. In certain embodiments, the detectable label comprises an optically detectable label. In certain embodiments, (d)(ii) comprises simultaneously adding a plurality nucleotide species that base-pair with four different nucleotide species in the polynucleotide features. In certain embodiments, each of the nucleotide species is distinguished from the other nucleotide species in the plurality of species by a distinct detectable label.

The details of one or more embodiments are set forth in the accompanying drawings and the description below. Other features, objects, and advantages will be apparent from the description and drawings, and from the claims.

BRIEF DESCRIPTION OF THE DRAWINGS

FIGS. 1A-B are schematics of four unique enzyme linked nucleotides according to an embodiment presented herein.

FIGS. 4A-C shows exemplary linkers, nucleotides and nucleotide incorporation of nucleotide-linkers according to embodiments presented herein.

DETAILED DESCRIPTION

Figure 1B:
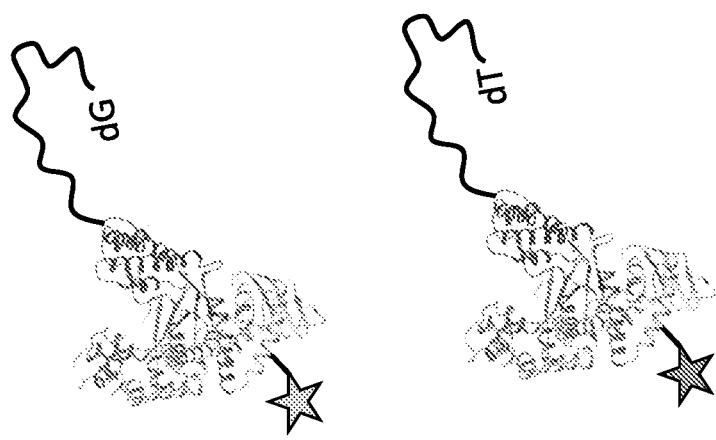

Presented herein are polymerase-linked nucleotides for improved distinguishing nucleotide sequences for different nucleic acid molecules. Also presented are methods and systems using the polymerase-linked nucleotides for improved distinguishing nucleotide sequences for different nucleic acid molecules.

The present disclosure provides a polymerase-linked nucleotide comprising a nucleotide covalently attached to a catalytically active polymerase enzyme by a flexible linker and methods of using the polymerase-linked nucleotides for detection of nucleotide sequences.

DNA polymerases perform DNA template dependent DNA polymerization with high fidelity. Coupling the polymerization process to a unique fluorescent signal for each of the four nucleotides can be used for DNA sequencing. Recent advances in sequencing chemistry have demonstrated that polymerization in high ionic conditions allows single nucleotide incorporation events followed by enzyme dissociation. See for example, the disclosure of U.S. application Ser. No. 13/722,979, entitled APPARATUS AND METHODS FOR KINETIC ANALYSIS AND DETERMINATION OF NUCLEIC ACID SEQUENCES, filed on Dec. 20, 2012, which is incorporated by reference in its entirety. Correct base calling under these increased ionic conditions is the result of an increased dwell time as the polymerase binds and incorporates correct dNTPs. Conversely, nucleotide flows containing mismatch for a given template cluster only display weak equilibrium binding in the absence of a correct dNTP. When coupled with a known nucleotide flow order, these two distinct binding patterns can be used to call nucleotide sequences using fluorescently labeled DNA polymerases.

DNA sequencing leveraging covalent linkage of DNA polymerase to its nucleotide substrate is a single molecule extension of the high ionic condition detection scheme to increase the rate of enzyme-DNA dissociation. As provided herein, nucleotide substrates are covalently attached to the enzyme through the use of commercially available linkers. Linker attachment to the nucleotide can occur at any position of the nucleotide which allows the nucleotide to be incorporated by the polymerase. In one embodiment, linker attachment to the nucleotide occurs on the 5' gamma phosphate. Attachment at this position can be advantageous for at least two reasons: 1) 5' gamma phosphate modifications to nucleotides can be correctly incorporated by polymerases; and 2) the product of catalysis with 5' gamma modified nucleotides is native DNA, leaving no modification behind. The nucleotide-linker molecule can contain a functional group that allows for site-specific conjugation to the polymerase surface and can contain additional phosphates to the 5' gamma phosphate.

Engineering enzyme linked nucleotides that are incorporated by the polymerase can be optimized using any of a variety of linker molecules as are known in the art. For example, many linker molecules are known which vary in length. In addition, any of a variety of different labeling positions on the surface of the polymerase may be used. For detection, each of the four enzyme-nucleotide complexes can be labeled with one of four unique dyes; producing color coded enzymes for each separate dNTP. The dye can be, for example, attached to the enzyme's surface distant from the nucleotide. Alternatively, the label can also part of the nucleotide substrate and/or linker.

DNA polymerase nucleotide affinity is governed by an apparent $K_d$ of 1-10 µM depending on the type of polymerase and the type of nucleotide. By linking the nucleotide to the polymerase the effective concentration of dNTP is increased due to nucleotide sequestration in proximity to the active site. Thus, the overall nucleotide concentration in solution can be equal to the enzyme concentration (e.g., ≤100 nM), while the effective concentration of the nucleotide can be tuned by changing the length of the linker.

Base calling can be accomplished by monitoring polymerase dwell time kinetics. Enzymes carrying an incorrect nucleotide bind to the DNA and rapidly dissociate, producing a short dwell time due to the lack of stabilization conferred by correct nucleotide binding. In contrast, enzymes carrying the correct nucleotide bind to the DNA and result in longer dwell times that include the kinetic steps nucleotide binding and catalysis. An example of this detection scheme is set forth in FIG. 2.

The enzyme linked nucleotide compositions and methods provided herein confer additional advantages in sequencing applications. For example, DNA sequencing can be performed with an optical detector and make use of "one pot" reactions that do not require flow. Single molecule detection can be performed, for example, using a light-based approach such as total internal reflection fluorescence (TIRF). TIRF detection can be optimized, for example, using nanomolar concentrations of fluorescent species to reduce the sample background. As a result, because the effective concentration of linked nucleotides to the polymerase is higher than the overall concentration of nucleotide (and labeled enzyme) background interference can be reduced while substrate concentration remains high.

An additional advantage is that chemistry using enzyme linked nucleotides does not require additional analysis to discriminate homopolymer sequence. DNA sequencing in the absence of 3' nucleotide blocking groups requires homopolymer discrimination based upon increased dwell time. Alternatively, the use of 3' blocks requires slow deblocking steps. Use of the enzyme linked nucleotides presented herein separates homopolymeric sequences into individual incorporation events because each polymerase can only incorporate its linked nucleotide. Successive polymerization requires dissociation of the nucleotide depleted enzyme and binding of nucleotide charged enzyme from solution. Thus, homopolymer incorporation will display as discrete events.

Figure 3A:
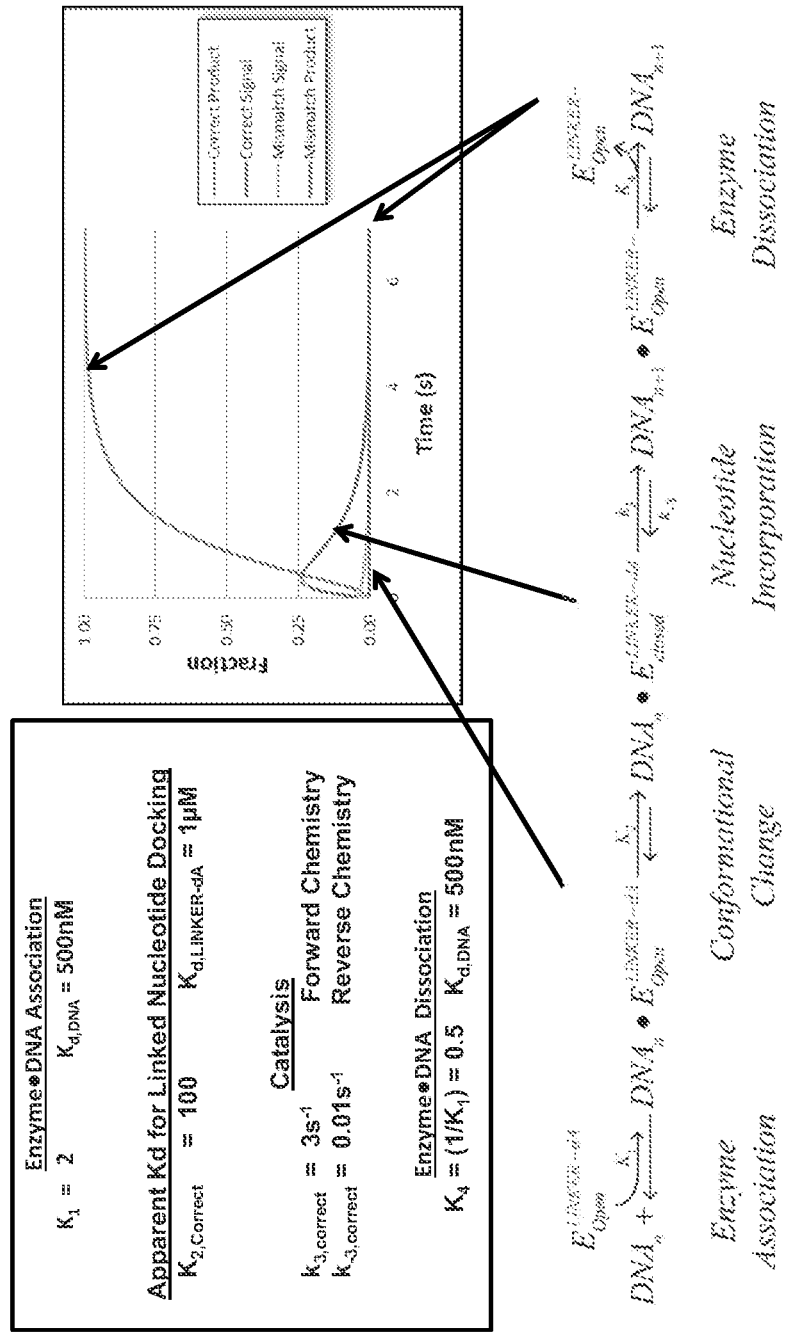
FIGS. 3A-C shows a time model of a polymerase incorporation cycle and the relationship between linker length and spherical concentration.
Figure 3B:
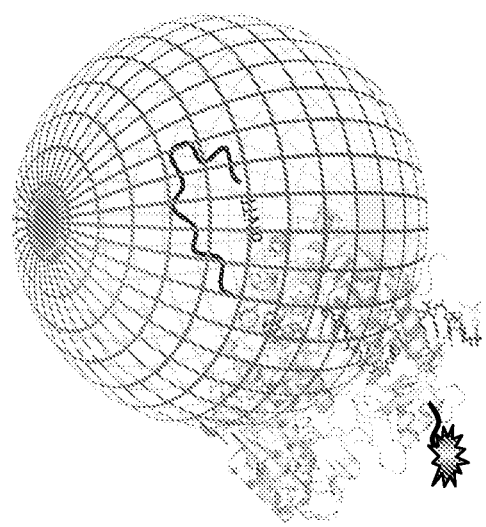
Figure 3C:
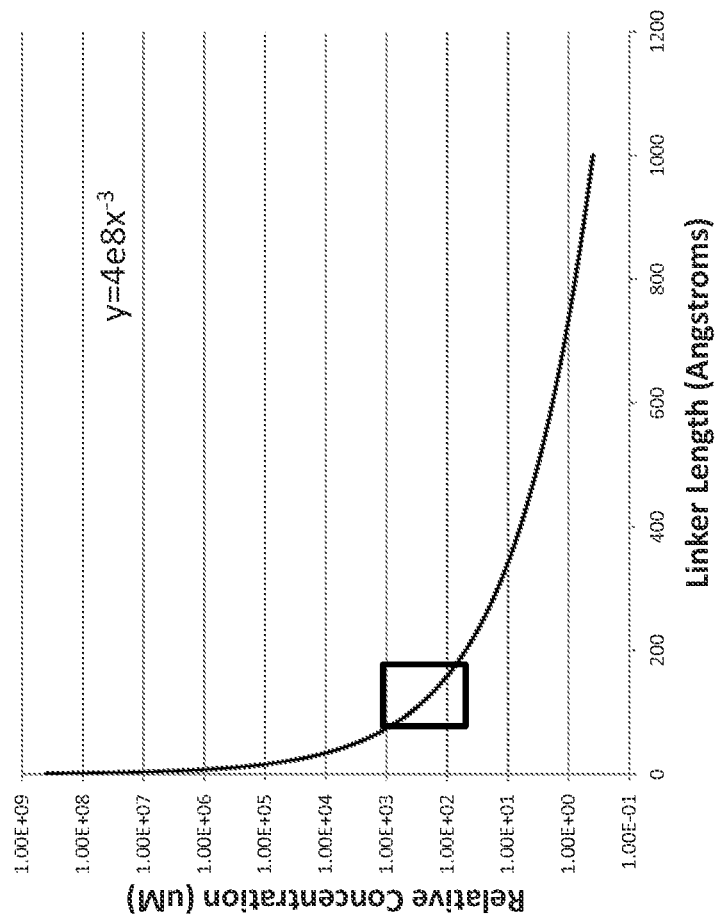

An additional advantage is that base calling can be performed on a second time-scale. Traditional single molecule sequencing must balance fast nucleotide incorporation with sufficient fluorescent lifetime to allow for detection. In contrast, the signal this method generates includes multiple kinetic steps (polymerase binding, nucleotide binding to the active site, and catalysis), ensuring that dwell time is sufficient for detection (FIG. 3). These multiple steps provide a sufficiently long dwell time to ensure incorporation events are not being missed by the frame rate of the detection camera. However, it will be appreciated that overall cycle times can be faster by optimizing polymerase structure, concentration of components and other aspects of the incorporation cycle.

An additional advantage is that the methods presented herein result in reduced branching ratios. Misincorporation and insertion/deletion errors can be advantageously reduced due to the absence of free nucleotide and pyrophosphate in solution.

An additional advantage is that the methods and compositions provided herein result in a cost-effective way to perform sequencing on a large scale. For example, bifunctional nucleotide linkers are commercially available and utilize aqueous reactions (thiol/maleimide, NHS-ester/Amine, alkeyne/azide). Additionally, "one pot" reactions require smaller volumes of reactants than flow systems, thereby reducing reagent use and cost.

Figure 1B:
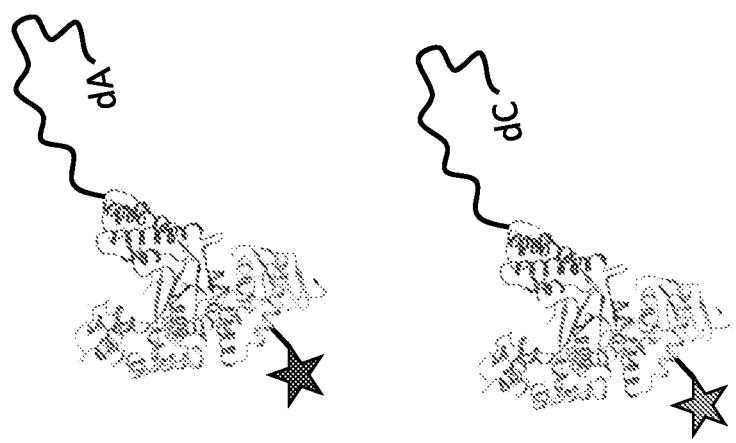

FIG. 1 depicts various a polymerase molecules covalently attached to a nucleotide through a flexible linker. Enzymes are also conjugated to a fluorescent dye that reports a unique color dependent upon the linked nucleotide (Red, dATP; Yellow, dGTP; Blue, dCTP; Green, dTTP; colors are examples only). Linker length and number of phosphates can be modified to optimize catalysis and discrimination of the correct nucleotide on a template strand.

Figure 2:
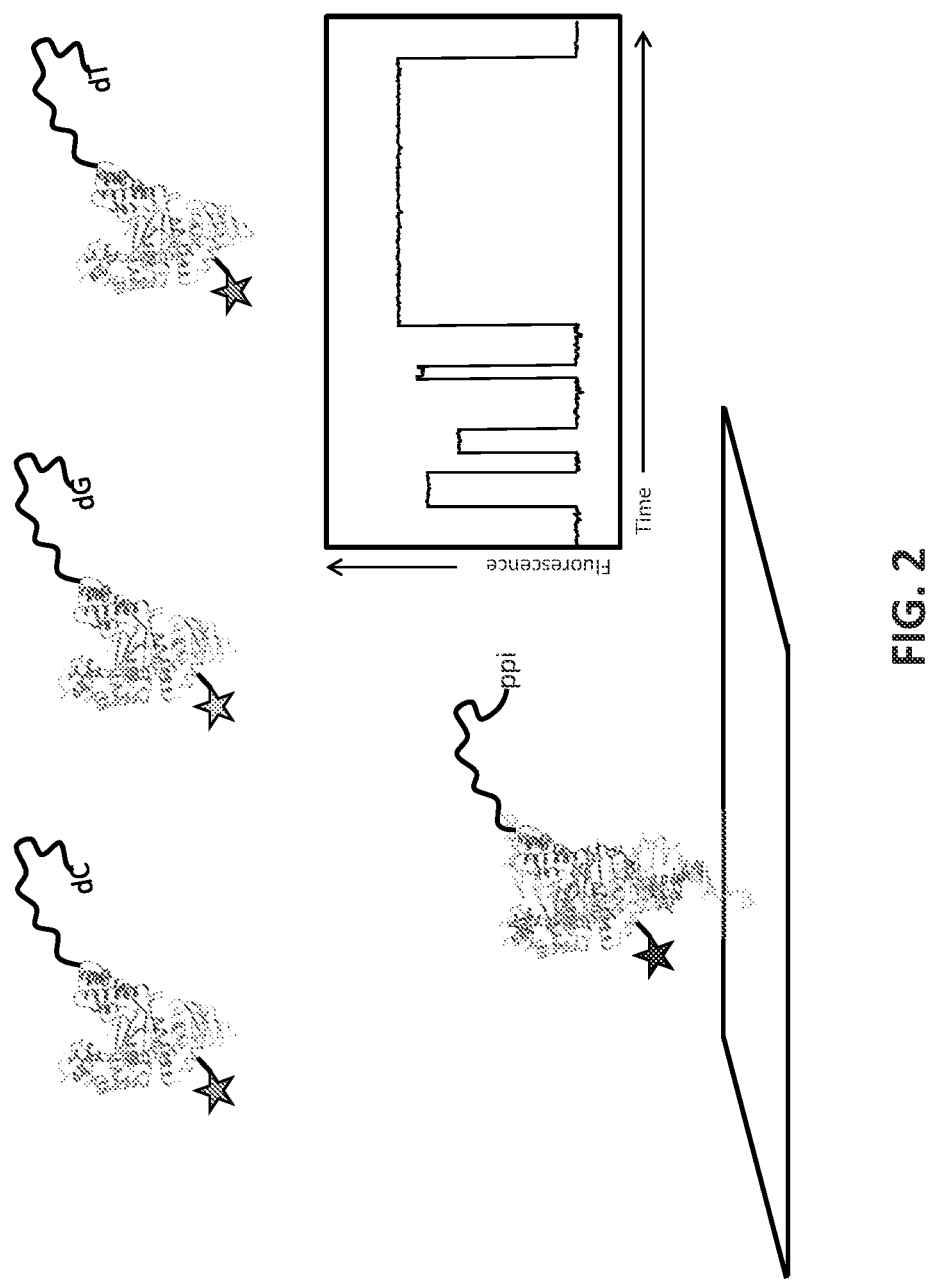
FIG. 2 is a schematic of a "one pot" single molecule sequencing using enzyme linked nucleotides according to an embodiment presented herein.

FIG. 2 depicts one embodiment where a TIRF field containing immobilized single molecule DNA strands can be overlayed with a reaction mixture containing four of the enzyme linked nucleotides with reporter dyes. (1) Free enzymes in solution can sample the target DNA with rapid binding and dissociation. (2) An enzyme linked to dATP will bind to the target DNA and incorporate the attached dATP resulting in a dwell time that is observed by the detection system. (3) Following incorporation the high ionic strength of the buffer promotes enzyme dissociation. The released enzyme contains no nucleotide and cannot catalyze additional incorporation events. The DNA product following nucleotide incorporation is natural DNA without modifications. This unmodified DNA then acts as the natural substrate for the next enzyme linked nucleotide incorporation event. As an additional advantage, the absence of free pyrophosphate prevents rive a reverse reaction from occurring.

A more detailed understanding of the compositions and methods of the present disclosure can be gained from the following definitions and exemplary embodiments.

Figure 4A:
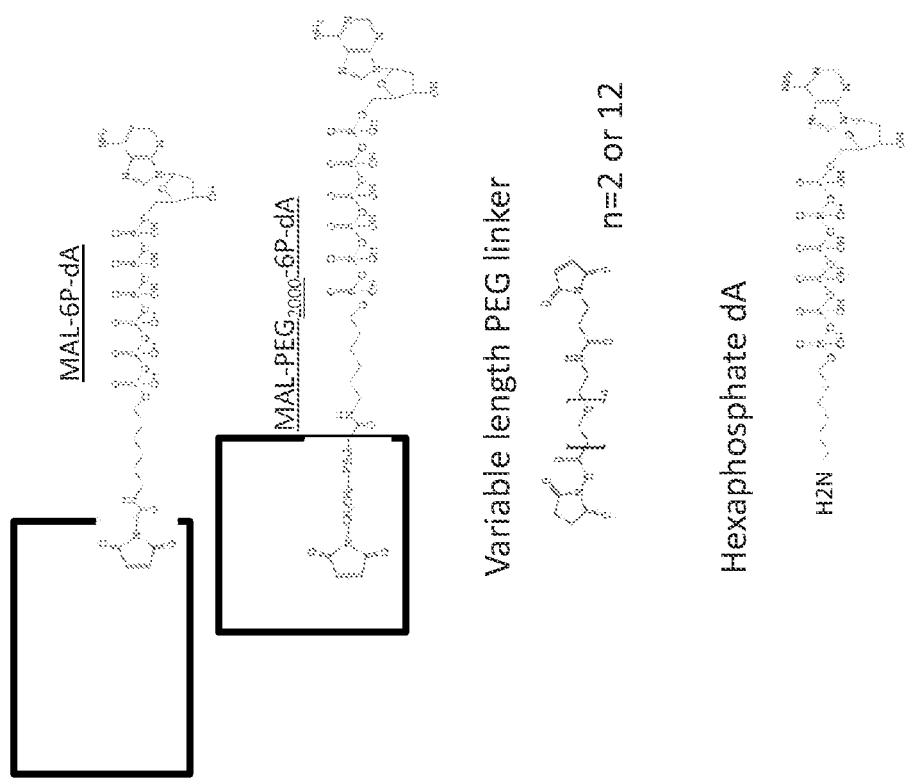
Figure 4B:
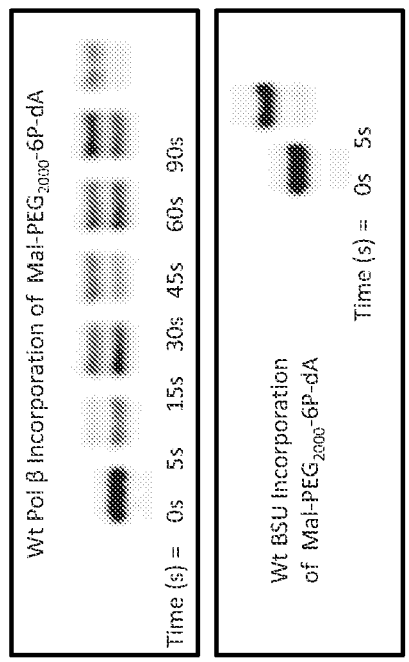

As used herein, the term "flexible linker" refers to a chemical group that is capable of covalently attaching a polymerase to a nucleotide or labeling moiety. In embodiments presented herein, the linker is reactive group that can be attached to a polymerase at one end and a nucleotide or labeling moiety. With regard to nucleotide attachment, the flexible linker is preferably selected to be flexible, hydrophilic, and of sufficient length that the attached nucleotide is freely accessible to the active site of the polymerase. The linker may be connected to the terminal phosphate of the nucleotide, or can be connected at any other suitable location on the nucleotide. Suitable flexible linkers are typically linear molecules in a chain of at least one or two atoms, more typically an organic polymer chain of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60 or more than 60 carbon atoms (and/or other backbone atoms) in length. Exemplary flexible linkers include polyethylene glycol (PEG), polypropylene glycol, polyethylene, polypropylene, polyamides, polyesters and the like, as exemplified in the disclosure of Krishnamurthy et al., (2007) J. Am. Chem. Soc., 129:1312-1320, which is incorporated by reference in its entirety. In certain aspects the flexible linker is a variable length PEG linker as depicted in FIG. 4. In some embodiments, the flexible linker has a length of greater than 50, 60, 70, 80, 90, 100, 110, 120, 130, 140, 150, 160, 170, 180, 190 or greater than 200 Angstrom. In some embodiments, the flexible linker has a length of less than 200, 190, 180, 170, 160, 150, 140, 130, 120, 110, 100, 90, 80, 70, 60 or less than 50 Angstrom.

As used herein, the term "surface-exposed residue" refers to an amino acid residue of the polymerase enzyme that has a side chain that is accessible on the surface of the molecule. In certain embodiments presented herein, one or more residues on the polymerase surface are used for conjugation of one or more the linker molecules. In some embodiments, a surface-exposed residue is mutated to cysteine to facilitate attachment of the linker molecule at the surface-exposed site.

As used herein, the term "relative concentration" refers to the concentration of a nucleotide molecule with respect to the area surrounding a polymerase molecule. In one embodiment, the relative concentration reflects the concentration of the nucleotide molecule within a spherical volume defined by the linker arm length as the radius of the sphere. In such embodiments, the relative concentration can be calculated as the moles of nucleotide per liters in the spherical volume. In some embodiments, the relative concentration of the nucleotide is greater than 1 µM, 10 µM, 100 µM, or greater than 1 mM. Additional concepts regarding relative concentration, effective molarity and effective concentration are known in the art as set forth in the incorporated materials of Krishnamurthy et al., (2007).

As used herein, the term "dwell time" refers to length of time a polymerase remains bound to a polynucleotide during a binding reaction. In some embodiments, the dwell time of a polymerase is a function of whether the nucleotide in the active site of the polymerase correctly base pairs with the template nucleotide. For example, enzymes carrying an incorrect nucleotide bind to the DNA and rapidly dissociate, producing a short dwell time due to the lack of stabilization conferred by correct nucleotide binding. In contrast, enzymes carrying the correct nucleotide bind to the DNA and result in longer dwell times that include the kinetic steps nucleotide binding and catalysis. An example of this detection scheme is set forth in FIG. 2.

As used herein, the term "binding," when used in reference to two molecules, means the process by which the molecules contact each other in a manner that results in a complex between the two molecules. The complex is typically reversible, for example, being mediated by non-covalent interactions. Accordingly binding can be characterized by association rates, dissociation rates and related kinetic parameters such as association rate constants and dissociation rate constants.

As used herein, the term "equilibrium," when used in reference to a reaction, means a state in which there is no net change in the amount of reactants or products of the reaction. For example, a binding reaction for a free polymerase and free nucleic acid that bind each other to form a polymerase-nucleic acid complex is at equilibrium when there is no net change in the amount of free polymerase, free nucleic acid and polymerase-nucleic acid complex.

As used herein, the terms "binding", "equilibrium", "pre-equilibrium (i.e. pre-steady state), "binding rate constant" (i.e. $k_1$, $k_{on}$ or association rate constant), "dissociation rate constant," (i.e. $k_{-1}$ or $k_{off}$) and "catalytic rate constant" (i.e. $k_{pol}$ or $k_{cat}$) are intended to be consistent with the meaning of the terms as they are known in the art, for example, as described in Segel, *Enzyme Kinetics* John Wiley and Sons, New York (1975), which is incorporated herein by reference in its entirety. These terms can be used to describe any of a variety of interactions that occur in a particular reaction between polymerase, nucleotide and nucleic acid. For example, the terms can be used to characterize pair-wise interactions that occur during association or dissociation of a larger complex such as the pair-wise interaction between polymerase and template nucleic acid in a complex that forms between the polymerase, template and a monomeric nucleotide. The terms can also characterize a combination or series of interactions such as interactions between polymerase, template nucleic acid and a nucleotide that form a ternary complex. The various interactions that can be characterized by the above kinetic terms will be evident from the description and equations set forth herein.

As used herein, the term "stopped-flow" means delivery of fluid to a detection site using rapid flow of the fluid followed by abrupt stoppage of the flow. The fluid that is delivered typically displaces an equal volume of fluid from the detection site. The fluid can mix with a solid-phase analyte. For example, a fluid containing polymerase molecules and/or nucleotide molecules can mix with a nucleic acid feature of an array, whereby the feature of the array is the detection site. In particular embodiments, two or more fluids can be mixed at a detection site. For example, a first fluid containing polymerase molecules and a second fluid containing nucleotide molecules can be mixed. The two or more fluids can optionally mix with a solid-phase analyte. For example, a first fluid containing polymerase molecules and a second fluid containing nucleotide molecules can be mixed at a detection site that contains a nucleic acid feature of an array. The dead time for stopped-flow fluid delivery can be, for example, less than 2 milliseconds (msec). Accordingly, the dead time can be no longer than 2 msec, 1.5 msec, 1 msec, 0.8 msec, 0.6 msec, 0.5 msec or 0.4 msec. See also Chance, B. J. *Frank. Inst.*, 229, 613 (1940), which is incorporated herein by reference in its entirety.

As used herein, the term "transient state," when used in reference to a polymerase, means the apparent condition or mode of the polymerase with respect to an interaction with another molecule. The interaction can be a binding interaction, a catalytic interaction or an interaction that includes both binding and catalysis. For example, a polymerase can be in a state whereby it is bound to a nucleic acid (e.g. at a feature of an array) or in a state where it is dissociated from a nucleic acid (e.g. at a feature of an array). It will be understood that a polymerase molecule can be dissociated from a nucleic acid feature despite being present in the same volume of solution occupied by the nucleic acid feature. Furthermore, reference to a polymerase being dissociated from a nucleic acid or other molecule does not necessarily imply that the polymerase was ever associated with the nucleic acid. The interaction is typically temporary or reversible and can be determined from a time based measurement. The transient state of a polymerase can be determined, for example, from a kinetic constant (e.g. binding rate constant, dissociation rate constant), an equilibrium constant, a reaction rate measurement, an equilibrium state measurement or the like. A transient state for a polymerase can also be determined as a combination of kinetic constants and therefore need not be defined by a single kinetic constant. The transient state of molecules other than polymerase shall be similarly defined as the apparent condition or mode of those molecules with respect to an interaction with another molecule.

As used herein, the term "transient dynamic," when used in reference to a polymerase (or other molecule), means an apparent change in an interaction of the polymerase (or other molecule) with another molecule. The interaction can be a binding interaction, a catalytic interaction or an interaction that includes both binding and catalysis. For example, the change can be the association of a polymerase with a nucleic acid (e.g. at a feature of an array) or dissociation of a polymerase from a nucleic acid (e.g. at a feature of an array). A transient dynamic of a polymerase can be determined, for example, from a kinetic constant (e.g. binding rate constant, dissociation rate constant), an equilibrium constant, a reaction rate measurement, an equilibrium state measurement or the like. A transient dynamic for a polymerase can be determined as a combination of kinetic constants and therefore need not be defined by a single kinetic constant.

As used herein, the term "correctly incorporate," when used in reference to a nucleotide and a nucleic acid, means that the nucleotide is covalently added to the nucleic acid in a template directed fashion in accordance with Watson-Crick base pairing to a nucleotide site in a template.

As used herein, the term "array" refers to a population of different molecules that are attached to one or more solid-phase substrates such that the different molecules can be differentiated from each other according to their relative location. An array can include different molecules that are each located at different addressable features on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be nucleic acid primers, nucleic acid probes, nucleic acid templates or nucleic acid enzymes such as polymerases, ligases or exonucleases.

As used herein, the term "feature" means a location in an array where a particular species of molecule is present. A feature can contain only a single molecule or it can contain a population of several molecules of the same species. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 µm. Medium density arrays have sites separated by about 15 to 30 µm, while low density arrays have sites separated by greater than 30 µm. An array useful herein can have, for example, sites that are separated by less than 100 µm, 50 µm, 10 µm, 5 µm, 1 µm, or 0.5 µm. An apparatus or method of the present disclosure can be used to detect an array at a resolution sufficient to distinguish sites at the above densities or density ranges.

As used herein, the term "species" is used to identify molecules according to their chemical structure. Two molecules that are the same species will have the same chemical structure and two molecules that are different species will have different chemical structures. For example, a mixture of nucleotides can include several dCTP molecules. The dCTP molecules will be understood to be the same species as each other. Similarly, individual DNA molecules that have the same sequence of nucleotides are the same species.

As used herein, the term "nucleic acid" can be used refer to at least two nucleotide monomers linked together. A nucleic acid can contain phosphodiester bonds, however, in some embodiments, a nucleic acid can be an analog having other types of backbones, comprising, for example, phosphoramide, phosphorothioate, phosphorodithioate, peptide nucleic acid backbones and linkages, positive backbones, or non-ionic backbones. A nucleic acid can include a pentose moiety such as ribose (present in naturally occurring RNA), deoxy-ribose (present in naturally occurring DNA) or dideoxy ribose. In some embodiments a nucleic acid can have a non-pentose moiety or carbocyclic sugar instead of a ribose or deoxyribose moiety. A nucleic acid can have one or more different base moieties including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Nucleic acids may be single stranded or double stranded, as specified, or contain portions of both double stranded and single stranded sequence. The nucleic acid may be DNA (e.g. genomic DNA or cDNA), RNA or a hybrid.

As used herein, the term "nucleotide" is intended to include natural nucleotides, non-natural nucleotides, ribonucleotides, deoxyribonucleotides, dideoxyribonucleotides and other molecules known as nucleotides. The term can be used to refer to a monomer unit that is present in a polymer, for example to identify a subunit present in a DNA or RNA strand. The term can also be used to refer to a molecule that is not necessarily present in a polymer, for example, a monomeric molecule that is capable of being incorporated into a polynucleotide in a template dependent manner by a polymerase. A nucleotide analog can have a base moiety including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include those that are not present in a natural biological system. A non-natural nucleotide can be incapable of being further extended after being incorporated into a polynucleotide. Examples include, nucleotides having a reversible or non reversible blocking moiety. In some embodiments, a nucleotide will not include a reversible blocking moiety, or a nucleotide will not include a non-reversible blocking moiety or a nucleotide will not include any blocking moiety at all. A natural or non-natural nucleotide can be capable of being further extended after being incorporated into a polynucleotide. Examples include, nucleotides having a 3' hydroxyl.

As used herein, the term "blocking moiety" when used in reference to a nucleotide, means a part of the nucleotide that inhibits or prevents the nucleotide from forming a covalent linkage to a second nucleotide. For example, in the case of nucleotides having a pentose moiety, a blocking moiety can prevent formation of a phosphodiester bond between the 3' oxygen of the nucleotide and the 5' phosphate of the second nucleotide. The blocking moiety can be part of a nucleotide that is a monomer unit present in a nucleic acid polymer or the blocking moiety can be a part of a free nucleotide (e.g. a nucleotide triphosphate). The blocking moiety that is part of a nucleotide can be reversible, such that the blocking moiety can be modified to render the nucleotide capable of forming a covalent linkage to a second nucleotide. In particular embodiments, a blocking moiety, such as a reversible blocking moiety, can be attached to the 3' position or 2' position of a pentose moiety of a nucleotide analog.

As used herein, the term "label" means a molecule or moiety thereof that provides a distinguishable characteristic. The distinguishable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like. The label can be part of a nucleotide that is a monomer unit present in a nucleic acid polymer or the label moiety can be a part of a free nucleotide (e.g. a nucleotide triphosphate).

The present disclosure provides a polymerase-linked nucleotide comprising a nucleotide covalently attached to a catalytically active polymerase enzyme by a flexible linker. In a certain embodiment, the linker attachment to the nucleotide allows the nucleotide to bind noncovalently at the active site of the polymerase. In a certain embodiment, the linker attachment to the nucleotide allows the polymerase to incorporate the nucleotide into the 3' end of a polynucleotide. In a certain embodiment, the polymerase comprises a detectable label, such as, for example a fluorophore.

The present disclosure also provides a modified polymerase comprising a pyrophosphate moiety at the terminal end of a flexible linker, the flexible linker covalently attached to a catalytically active polymerase, the composition being formed by the incorporation of a nucleotide into the 3' end of a polynucleotide by the polymerase. In a certain embodiment, the linker attachment to the nucleotide allows the nucleotide to bind noncovalently at the active site of the polymerase. In a certain embodiment, the linker attachment to the nucleotide allows the polymerase to incorporate the nucleotide into the 3' end of a polynucleotide.

The present disclosure also provides a method of distinguishing nucleotide sequences for different nucleic acid molecules, comprising (a) providing a plurality of different nucleic acid molecules, wherein the different nucleic acid molecules are attached to a surface in the form of an array of nucleic acid features; (b) adding a plurality of polymerase-linked nucleotides to the nucleic acid features, (c) monitoring binding of the polymerase molecules to the nucleic acid features, thereby determining dwell time of the polymerase molecules at the nucleic acid features; and (d) identifying nucleic acid features of the array that correctly incorporate the nucleotide molecules based on the dwell time of the polymerase molecules at the nucleic acid features, thereby distinguishing the nucleotide sequences for the different nucleic acid molecules. In certain embodiments, (b) comprises monitoring a detectable signal indicative of the binding of the polymerase molecules to the nucleic acid features and catalysis of nucleotide incorporation into the polynucleotide feature. In certain embodiments, (c) comprises identifying the nucleic acid features of the array that correctly incorporate the nucleotide molecules based on detectable signal of the polymerase molecules at the nucleic acid features, whereby the dwell time determines nucleotide molecules that are correctly incorporated into the nucleic acid features, thereby distinguishing the nucleotide sequences for the different nucleic acid molecules. In certain embodiments, (b) comprises simultaneously adding a plurality nucleotide species that base-pair with four different nucleotide species in the polynucleotide features. In certain embodiments, each of the nucleotide species is distinguished from the other nucleotide species in the plurality of species by a distinct detectable label.

The present disclosure also provides a system for distinguishing nucleotide sequences for different nucleic acid molecules, the system comprising (a) an array comprising nucleic acid features having different nucleotide sequences; (b) a fluidic apparatus configured to deliver sequencing reagents to the array, wherein the sequencing reagents comprise polymerase-linked nucleotide comprising a nucleotide covalently attached to a catalytically active polymerase enzyme by a flexible linker; (c) a detection apparatus configured to measure binding events from the array at a resolution that distinguishes individual nucleic acid features of the array; and (d) a control module comprising instructions for (i) adding the sequencing reagents to the nucleic acid features, (ii) obtaining measurements of binding of the polymerase molecules to the nucleic acid features; and (e) an analysis module comprising instructions for (i) processing the measurements of binding of the polymerase molecules to the nucleic acid features, thereby determining dwell time of the polymerase molecules at the nucleic acid features; and (ii) identifying nucleic acid features of the array that correctly incorporate the nucleotide molecules based on the dwell time of the polymerase molecules at the nucleic acid features, thereby distinguishing the nucleotide sequences for the different nucleic acid molecules. In certain embodiments, (d)(ii) comprises monitoring a detectable signal indicative of the binding of the polymerase molecules to the nucleic acid features and catalysis of nucleotide incorporation into the polynucleotide feature. In certain embodiments, (e)(ii) comprises identifying the nucleic acid features of the array that correctly incorporate the nucleotide molecules based on detectable signal of the polymerase molecules at the nucleic acid features, whereby the dwell time determines nucleotide molecules that are correctly incorporated into the nucleic acid features, thereby distinguishing the nucleotide sequences for the different nucleic acid molecules. In certain embodiments, (d)(ii) comprises monitoring a detectable signal indicative of the binding of the polymerase molecules to the nucleic acid features and catalysis of nucleotide incorporation into the polynucleotide feature. In certain embodiments, the detectable label comprises a detectable label attached to the polymerase. In certain embodiments, the detectable label comprises an optically detectable label. In certain embodiments, (d)(ii) comprises simultaneously adding a plurality nucleotide species that base-pair with four different nucleotide species in the polynucleotide features. In certain embodiments, each of the nucleotide species is distinguished from the other nucleotide species in the plurality of species by a distinct detectable label.

For ease of explanation, reaction components are referred to above and elsewhere herein in the singular. It will be understood however that unless the context clearly indicates otherwise, those methods and compositions that are described using the singular also encompass the plural. For example, the description above of delivering a polymerase is intended to describe delivery of one or more polymerase molecules.

The component(s) at the reaction site can be in solution or attached to a solid phase surface. For example, the nucleic acid component can be attached to a feature of an array. Thus, mixing can occur between solution-phase component(s) and solid-phase component(s). A reaction component can be attached to an array in a way that provides detection at a single molecule level or at an ensemble level. Single molecule detection can be achieved with a population of reaction components that is attached to a solid support in a way that signals arising from an individual reaction component can be distinguished from signals arising from all other reaction components on the support. Ensemble level detection can be carried out such that a population of nucleic acids (or other reaction components) is attached at a feature of an array in a way that reactions occurring for several molecules at the feature can be detected. In ensemble-level detection reactions occurring for several species within a feature need not be distinguished from each other, but reactions occurring at different features on the same array can be distinguished from each other.

In some embodiments, a plurality of nucleic acid molecules is present at an individual feature and each molecule contains an individual template. Examples of such arrays are those produced by solid-phase amplification methods such as the clustering methods (also known as bridge amplification) or emulsion PCR methods set forth herein below. For embodiments where individual nucleic acid molecules each contain individual templates, the spacing between the surface attachment points for the molecules can be, for example, at most about 500 nm, 100 nm, 50 nm, 10 nm, 5 nm, 1 nm or lower. Template spacing in solid-phase amplification methods can be controlled, for example, by varying the surface concentration of primers used for capture and/or amplification of the templates (e.g. varying the concentration of primers on a flow cell used for bridge amplification or varying the concentration of primers on beads used for emulsion PCR). More specifically, surfaces having higher template densities can be obtained by grafting the surfaces with higher concentrations of the primers, thereby decreasing the spacing between templates.

Embodiments are also provided where a plurality of templates are present on a single nucleic acid molecule. For example, a concatameric amplicon that is produced by a rolling circle amplification method can include several copies of a particular template. Rolling circle amplification (RCA) can be carried out as described, for example in Lizardi et al., *Nat. Genet.* 19:225-232 (1998) or US 2007/0099208 A1, each of which is incorporated herein by reference in its entirety. A nucleic acid molecule that has several template copies, whether produced by RCA or another method, can be attached to a surface. The surface can be for example, a feature of an array and the feature can contain one or more of the nucleic acid molecules that have several template copies.

Any of a variety of polymerases can be used in a method or composition set forth herein including, for example, protein-based enzymes isolated from biological systems and functional variants thereof. Generally, polymerases that display a relatively large difference between the $k_{-1}$ (or $k_{off}$) for a correct nucleotide and mismatched nucleotides (with respect to Watson-Crick base pairing to a template) are desirable. When using ensemble level detection, good base discrimination can be achieved by maximizing the diffusion rate, $k_{-1}$ and $k_1$ (or $k_{on}$). Examples of desirable polymerases are family A polymerases, such as Klenow fragment of E. coli DNA polymerase I, family B polymerases, such as apo protein of T4 & Rb69 polymerases, and family X polymerases such as pol beta since these polymerases demonstrate relatively poor processivity (i.e. small $k_1$). Reduction in processivity can also be achieved through manipulation of sequencing conditions such as buffer conditions, ionic strength, mixed metal ions, elevated reaction temperatures, crowding reagents (e.g. polyethylene glycol), detergents and/or pH.

Reference to a particular polymerase will be understood to include functional variants thereof unless indicated otherwise. A particularly useful function of a polymerase is the ability to bind to a nucleic acid and nucleotide to form a complex and the ability to catalyze the extension of the nucleic acid strand by addition of the nucleotide. Other polymerase functions that are useful are described elsewhere herein. Examples of useful polymerases include DNA polymerases and RNA polymerases. Exemplary DNA polymerases include those that have been classified by structural homology into families identified as A, B, C, D, X, Y, and RT. DNA Polymerases in Family A include, for example, T3, T5 or T7 DNA polymerases, eukaryotic mitochondrial DNA Polymerase γ, E. coli DNA Pol I, Thermus aquaticus Pol I, Bacillus subtilis Pol I and Bacillus stearothermophilus Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase. Family C includes, for example, the E. coli DNA Polymerase III alpha subunit. Family D includes, for example, polymerases derived from the Euryarchaeota subdomain of Archaea. DNA Polymerases in Family X include, for example, eukaryotic polymerases Pol β, pol λ, and Pol μ, and S. cerevisiae Pol4. DNA Polymerases in Family Y include, for example, Pol η, Pol iota, Pol kappa, E. coli Pol IV (DINB) and E. coli Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

The above classifications are provided for illustrative purposes. It will be understood that variations in the classification system are possible. For example, in at least one classification system, Family C polymerases have been categorized as a subcategory of Family X. Furthermore, polymerases can be classified according to other characteristics, whether functional or structural, that may or may not overlap with the structural characteristics exemplified above. Some exemplary characteristics are set forth in further detail below.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein. Polymerases can also catalyze pyrophosphorolysis, the direct reversal of polymerization in the same active site. This activity can be useful for various embodiments that are set forth herein.

Polymerases can be characterized according to their processivity. A polymerase can have an average processivity that is at least about 50 nucleotides, 100 nucleotides, 1,000 nucleotides, 10,000 nucleotides, 100,000 nucleotides or more. Alternatively or additionally, the average processivity for a polymerase used as set forth herein can be, for example, at most 1 million nucleotides, 100,000 nucleotides, 10,000 nucleotides, 1,000 nucleotides, 100 nucleotides or 50 nucleotides. Polymerases can also be characterized according to their rate of processivity or nucleotide incorporation. For example, many native polymerases can incorporate nucleotides at a rate of at least 1,000 nucleotides per second. In some embodiments a slower rate may be desired. For example, an appropriate polymerase and reaction conditions can be used to achieve an average rate of at most 500 nucleotides per second, 100 nucleotides per second, 10 nucleotides per second, 1 nucleotide per second, 1 nucleotide per 10 seconds, 1 nucleotide per minute or slower. It will be understood that polymerases from any of a variety of sources can be modified to increase or decrease their average processivity or their average rate of processivity (e.g. average rate of nucleotide incorporation) or both. Accordingly, a desired reaction rate can be achieved using appropriate polymerase(s), nucleotide analog(s), nucleic acid template (s) and other reaction conditions.

A polymerase can be either thermophilic or heat inactivatable (e.g. at a temperature that falls in the range of 40° C. to 90° C. Thermophilic polymerases are typically useful for high temperature conditions or in thermocycling conditions such as those employed for polymerase chain reaction (PCR) techniques. Examples of thermophilic polymerases include, but are not limited to, 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. Polymerases from any of a variety of sources can be modified to increase or decrease their tolerance to high temperature conditions for use in a method or composition set forth herein.

Polymerases can be characterized according to their fidelity. Fidelity generally refers to the accuracy with which a polymerase incorporates correct nucleotides into a copy of a nucleic acid template. DNA polymerase fidelity can be measured as the ratio of correct to incorrect nucleotide incorporations when the nucleotides are present at equal concentrations to compete for primer extension at the same site in the polymerase-primer-template DNA binary complex. As proposed by Fersht, DNA polymerase fidelity can be calculated as the ratio of $(k_{cat}/K_m)$ for the correct nucleotide and $(k_{cat}/K_m)$ for the incorrect nucleotide; where $k_{cat}$ and $K_m$ are the familiar Michaelis-Menten parameters in steady state enzyme kinetics (Fersht, A. R. (1985) *Enzyme Structure and Mechanism*, 2nd ed., p 350, W. H. Freeman & Co., New York, which is incorporated herein by reference in its entirety). Alternatively, in pre-equilibrium measurements, the ratio of ($k_{pol}/K_d$) for the correct and incorrect nucleotides can be used. In particular embodiments, a polymerase can have a fidelity value at least 100, 1000, 10,000, 100,000, or 1 million, with or without a proofreading activity.

A polymerase that is used in a method or composition herein can include a label. Fluorophores are particularly useful for labeling polymerases, but can be used for other reaction components set forth herein as well. Exemplary fluorophores include, but are not limited to, fluorescent nanocrystals; quantum dots; d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorescent probes and methods for their use including attachment to polymerases and other molecules are described in *Molecular Probes: The Handbook* (Invitrogen, Carlsbad Calif.), which is incorporated herein by reference in its entirety. A fluorophore or other probe that is used in a method or composition set forth herein can be an intrinsic probe that is present in a naturally occurring molecule being detected, such as a tryptophan residue in a polymerase. Alternatively or additionally, one can use a probe that is exogenous to a polymerase or other molecule being detected. Thus, in some embodiments solely exogenous probes are detected such that endogenous probes are not detected, in other embodiments solely endogenous probes are detected such that exogenous probes are not detected and in some embodiments a combination of exogenous and endogenous probes are detected.

In particular embodiments, a green fluorescent (GFP) protein can be attached to a polymerase. GFP can be attached via a chemical linkage, or in many cases more conveniently via a protein fusion. Protein fusions have a polypeptide linkage between a GFP domain and polymerase domain formed by expression from a genetic construct where the coding sequences of the two domains are fused. Variants of GFP such as wavelength shifted variants can be used similarly. Techniques for making and using GFP and variants thereof are described throughout *Chemical Society Reviews* volume 38, issue 10 (2009), which is incorporated herein by reference in its entirety.

A label can be attached to a polymerase or other reaction component, for example, via covalent linkage. In a particular embodiment, a probe can be attached site specifically to a polymerase by introducing cysteine residue at a desired location in the polymerase and then modifying the polymerase with a probe having a moiety that reacts specifically with the sulfur group of cysteine, an exemplary reactive moiety being a reactive maleimide moiety. An exemplary method for introducing probes into a polymerase using site specific cysteine mutagenesis followed by chemical modification with dyes having maleimide moieties is described in Santoso et al. *Proc. Nat'l. Acad. Sci. USA* 107:705-710 (2010), which is incorporated herein by reference in its entirety. Probes can also be introduced to polymerase by split inteins as described in Yang et al. *J. Am. Chem. Soc.*, 131:11644-11645 (2009), which is incorporated herein by reference in its entirety. Probes can also be introduced to a polymerase by genetically encoded unnatural amino acids. One example is described in Fleissner et al. *Proc. Nat'l. Acad. Sci. USA* 106:21637-42 (2009), which is incorporated herein by reference in its entirety.

Labels other than fluorescent labels can be used. For example, a polymerase or other reaction component can be labeled by paramagnetic spin labels such as nitroxide, and detected by electron paramagnetic resonance and related techniques. Exemplary spin labels and techniques for their detection are described in Hubbell et al. *Trends Biochem Sci.* 27:288-95 (2002), which is incorporated herein by reference in its entirety. Gold nanoparticles with thiol reactive groups can also be used to label proteins, for example as described in Gregori et al. *J. Biol. Chem.* 272:58-62 (1997), which is incorporated herein by reference in its entirety.

Electrical based detection can be used. Electrical detection is particularly useful for a field use (e.g. hand held) sequencing device. Electrical detection is advantageous because it does not require light sources, optics and protein labels. Field effect transistors (FET), a class of biosensors, can be used for electrical detection, for example as described in Schöning and Poghossian, *Analyst,* 127: 1137-1151 (2002), which is incorporated herein by reference in its entirety. FET biosensors respond to change in local charge distribution. Ion sensitive field effect transistors (ISFETs) are a type of FET that can be used, for example, as described in Bergveld, *IEEE Trans. Biomed. Eng.,* 17, 70-71 (1970), which is incorporated herein by reference in its entirety. ISFETs are especially optimized for pH sensing; thus, they are ideal sensors for monitoring enzymatic reactions that generate protons as a product. Changes in intrinsic surface charge lead to a change in the local charge distribution that can be detected, for example, as described in Schenck, *Theory, Design and Biomedical Applications of Solid State Chemical Sensors*, ed. P. W. Cheung, CRC Press, Boca Raton, 1978, pp. 165-173, which is incorporated herein by reference in its entirety. FETs have been advanced with silicon nanowire (SiNW) and carbon nanotube (CNT) devices and can be used for electrical detection as described in Cui et al., *Science,* 293: 1289-1292 (2001), which is incorporated herein by reference in its entirety. Femtomolar sensitivity with SiNW FETs can be accomplished by detecting in the frequency domain instead of the time domain as described by Zheng et al., *NanoLett.* 10(80):3179-3183, which is incorporated herein by reference in its entirety. Single molecule sensitivity can be achieved on CNT with microsecond resolution as described by Sorgenfrie et al. *Nat. Nano.,* 6:126-132 (2011), which is incorporated herein by reference in its entirety.

In one embodiment DNA can be covalently attached to SiNW and CNTs for FET based detection of the transient polymerase kinetics. A second method of electrical detection can exploit electron transport through gold nanoparticles. Direct electron transport through gold nanoparticles can be readily measured, for example, as described in Nakanishi et al., *Nat. Nano.* 6:740-746 (2011), which is incorporated herein by reference in its entirety. In one embodiment, DNA can be immobilized between two electrodes. Electron transport will occur during the polymerase transient binding events. The polymerase will be conjugated to gold nanoparticles; thus, the amount of current will correspond to the transient polymerase binding kinetics.

Label-free sensing can also be used in a method set forth herein. Examples include, but are not limited to, sensing techniques related to a change in the environment and/or the size of a nucleic acid feature (whether an ensemble feature or single molecule feature) upon binding of polymerase.

Any of a variety of nucleotide species can be useful in a method or composition set forth herein. For example, naturally occurring nucleotides can be used such as ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Typically, dNTP nucleotides are incorporated into a DNA strand by DNA polymerases and NTP nucleotides are incorporated into an RNA strand by RNA polymerases. In particular embodiments, NTP nucleotides or analogs thereof can be incorporated into DNA by a DNA polymerase, for example, in cases where the NTP, or analog thereof, is capable of being incorporated into the DNA by the DNA polymerase and where the transient state (or the transient dynamic) of the DNA polymerase on the DNA in the presence of an NTP that properly base pairs with the DNA can be distinguished from the transient state (or the transient dynamic) of the polymerase in the presence of a mismatched nucleotide. Alternatively, dNTP nucleotides or analogs thereof can be incorporated into RNA by an RNA polymerase, for example, in cases where the dNTP, or analog thereof, is capable of being incorporated into the RNA by the RNA polymerase and where the transient state (or the transient dynamic) for the RNA polymerase in the presence of a correctly matched dNTP can be distinguished from the transient state (or the transient dynamic) of the RNA polymerase in the presence of a mismatched nucleotide.

Non-natural nucleotide analogs are also useful. Particularly useful non-natural nucleotide analogs include, but are not limited to, those for which polymerase displays a transient state (or a transient dynamic) that is distinguishable with respect to correctly matched and mismatched base moieties. For example, a non-natural nucleotide analog having a base moiety that correctly base pairs with a template strand may usefully produce a detectably different transient state (or transient dynamic) for a polymerase compared to the transient state (or the transient dynamic) for the polymerase in the presence of a nucleotide analog having a base moiety that does not correctly match with the template.

Non-natural nucleotide analogs having 5' modifications are particularly useful. The non-natural nucleotide analog will typically have a triphosphate but can have more or fewer phosphates as set forth elsewhere herein. In particular embodiments, one or more of the alpha phosphate, beta phosphate or gamma phosphate of a non-natural nucleotide is covalently attached to a moiety other than oxygen. A moiety that is attached to a phosphate or otherwise present at the 5' position can provide a negative charge, a positive charge, metal-chelating activity or steric bulk. Exemplary moieties include, but are not limited to, amino acids, in the L-enantiomer form or R-enantiomer form, such as histidine, aspartate, glutamate, tryptophan, phenylalanine, methionine, tyrosine, cysteine, glycine alanine, or proline; an amino group; a chelated metal such as magnesium or manganese; a methyl group; a halogen such as bromine, chlorine or iodine; a thiol group; an electron withdrawing group; an electron donating group; an aromatic amine; or an aliphatic amine. These and other moieties may be advantageous in embodiments where they provide an interaction with a polymerase, or other nucleic acid enzyme, that differs from the interaction that the enzyme has with a nucleotide lacking the moiety. As such, the presence and absence of the moiety on respective nucleotide species can be exploited to distinguish the nucleotide species in a sequencing method, for example, based on the transient state (or the transient dynamic) of the polymerase with respect to interactions with a template nucleic acid in the presence of the nucleotide species.

It will be understood that the 3' position of a nucleotide can have a blocking moiety (such as a reversible blocking moiety) or other moiety. Examples of reversible blocking moieties that can be used and their respective deblocking agents are described, for example, in U.S. Pat. Nos. 7,427,673; 7,414,116; 7,057,026 and 8,241,573; and PCT publications WO 91/06678 and WO 07/123744, each of which is incorporated herein by reference in its entirety. For methods that use reversibly blocked nucleotides, deblocking and washing steps can be carried out between nucleotide addition steps. Typically a chemically reactive deblocking moiety is used; however a photo-sensitive block can be used for fast deblocking by light. It will be understood that in some embodiments a nucleotide analog having a 3' blocking moiety or lacking a 3' hydroxyl (such as a dideoxynucleotide analog) can be used under conditions where the primer strand that has incorporated the nucleotide analog is not further extended. In some embodiments, the nucleotide(s) will not include a reversible blocking moiety, or the nucleotides(s) will not include a non-reversible blocking moiety or the nucleotide(s) will not include any blocking moiety at all.

Another useful type of nucleotide is a caged nucleotide. An exemplary caged nucleotide has a moiety with a photo-isomerizable double bond. In particular embodiments, a first isomer of the caged nucleotide causes a polymerase to have a different transient state (or transient dynamic) for a nucleic acid template than occurs in the presence of a second isomer of the caged nucleotide. For example, a polymerase may readily bind to a template nucleic acid in the presence of the first isomer under particular conditions whereas the polymerase will not appreciably bind to the nucleic acid template in the presence of the second isomer under the particular conditions. Azobenzene is a moiety that undergoes photo-isomerization whereby UV radiation causes trans to cis conversion and blue light causes cis to trans conversion. Other moieties that undergo photo-isomerization and conditions for their photo-isomerization are known in the art and include, for example, stilbene, and cinnamic acid.

A further example of a caged nucleotide is one having a moiety that is photo-cleavable. In some embodiments, the presence of the moiety on the nucleotide alters (e.g. reduces or increases) the rate of binding or catalysis of a polymerase for a nucleic acid template compared to the nucleotide without the moiety. For example, a polymerase may readily bind to a nucleic acid template in the presence of a nucleotide lacking the moiety under particular conditions whereas the presence of the moiety will retard or prevent the polymerase from binding to the nucleic acid under the particular conditions. Exemplary photo-cleavable moieties include, but are not limited to (1-(4,5-dimethoxy-2-nitrophenyl) ethyl) ester (i.e. DMNPE) and (1-(2-nitrophenyl) ethyl) ester (i.e. NPE). See *Meth. Enzymol.* 291:307-347 (1998), which is incorporated herein by reference in its entirety.

A photo-isomerizable moiety or photo-cleavable moiety can be attached to a nucleotide at any of a variety of locations in the nucleotide including, but not limited to, the ribose moiety, a phosphate moiety, or a base moiety or other specific locations exemplified herein in the context of other nucleotide analogs. Furthermore, a photo-isomerizable moiety or photo-cleavable moiety can be attached to one or more nucleotide species used in a method or reaction set forth herein. For example, such moieties can be present on a nucleotide analog having a base moiety that pairs with adenine, thymine, guanine or cytosine. Mixtures of nucleotides can be used that have different photo-isomerizable or photo-cleavable moieties. Such a mixture can further include one or more nucleotides having no photo-reactive moiety. The different moieties can be tuned for photoreactions with different wavelengths of light. As such, individual nucleotide species can be activated (or deactivated) using different wavelengths of light in order to provide light-gated control of individual nucleotide species in a reaction such as a sequencing reaction set forth herein.

Use of one or more caged nucleotide species can provide a means to initiate, modulate or attenuate a reaction set forth herein. For example, one or more photo-isomerizable or photo-cleavable nucleotide species can be introduced to a reaction in an inactive conformation and subsequently light activation can be used to initiate binding of nucleotides to a polymerase or addition of the nucleotides to a nucleic acid by a polymerase. Thus, light activation can provide temporal control of the start point for a reaction set forth herein. Alternatively or additionally, photo-isomerizable nucleotides that are in an active conformation can be inactivated by light to pause or stop a polymerization reaction. Stopping a reaction can be achieved by separating reaction components from each other, for example by washing the nucleotides away from a solid-phase attached nucleic acid. Such a separation step need not be carried out and instead the reaction can be resumed by toggling the photo-isomerizable nucleotide to an active form to resume polymerization. As such, caged nucleotides provide a means to achieve light-gated control of a variety of reactions such as the sequencing methods set forth herein.

Light-gating is particularly useful for embodiments that use real-time detection at a single molecule level. Single molecule reactions are stochastic by nature. Light-gating provides for temporal control of detection to coincide with initiation of the single molecule reaction thereby providing more accurate detection.

Although an advantage of light-gating is set forth above in regard to real-time detection at a single molecule level, it will be understood that light gating is also useful for ensemble-level detection. For example, whether used for a single-molecule or ensemble level embodiments, light gating can provide spatial or temporal control of a reaction. More specifically, a sample can contain a relatively large pool of nucleotides and focused light can be delivered to a portion of a sample to activate a sub-population of the nucleotides. Thus, repeated activation of a subpopulation of nucleotides can be used instead of repeated fluidic delivery steps.

Variants of polymerase can be engineered to bind to and/or catalytically react with natural or non-natural nucleotides at an appropriate or otherwise desired speed to allow detection of differences in polymerase interactions with nucleic acid when different nucleotides are used.

In some embodiments, a reaction composition or method can include a plurality of nucleotide species that base-pair with all nucleotide species in a nucleic acid template. Additionally or alternatively, a reaction composition or method can include all nucleotide species that base-pair with no more than one nucleotide species in a nucleic acid template. For example, a method can be carried out under conditions wherein different nucleotide species are contacted with a polymerase and nucleic acid in separate, sequential reactions. Specifically, a nucleotide species that base-pairs with only A can be added in a first reaction, a nucleotide species that base-pairs with only C can be added in a second reaction, a nucleotide species that base-pairs with only T can be added in a third reaction, and a nucleotide species that base-pairs with only G can be added in a fourth reaction. The reactions are referred to as first, second, third and fourth merely to illustrate that the reactions are separate but this does not necessarily limit the order by which the different nucleotide species can added in a method set forth herein. Rather, nucleotide species that base-pair with A, C, T or G can be added in any order desired or appropriate for a particular embodiment of the methods. Typically in a sequencing method, one or more nucleotide species that base-pair with four different nucleotide species in a given template nucleic acid are added sequentially to complete a cycle of the sequencing method. However, it will be understood that fewer than four nucleotide additions can be used in some embodiments. Furthermore, it will be understood that mixtures of nucleotides that base-pair with more than one but no more than 2, 3 or 4 nucleotide species in the nucleic acid template(s) of a sample can be used. Similarly, mixtures of nucleotides that base-pair with more than two but no more than 3 or 4 nucleotide species in the nucleic acid template(s) of a sample can be used. If desired, mixtures of nucleotides that base-pair with more than three but no more than 4 nucleotide species in the nucleic acid template(s) of a sample can be used.

One or more of the reaction components that are used in a method set forth herein can include a label. For example, as set forth previously herein, a polymerase can include a label and the label can be detected during a binding or other reaction. The labels and associated detection methods set forth previously herein in regard to polymerases can be used for other reaction components, for example, as set forth below. In some embodiments, a nucleotide that is used in a binding or other reaction can contain a label that is detected during the reaction. Similarly, a label can be present on a nucleic acid template that binds to a polymerase. It is also useful in some cases to include a label on two or more of the components of a particular reaction. For example, labels can be present on both a nucleotide and a polymerase that participate in a binding or other reaction. Either or both of the labels can be detected to determine transient state (or transient dynamic) of the polymerase with respect to binding or catalytic interactions with a nucleic acid template. Labels can be used that interact with each other to give a characteristic signal when polymerase is bound to a nucleic acid (e.g. a nucleic acid template present at a feature of an array). For example, the labels can provide a donor and acceptor pair for a FRET interaction or a fluorophore and quencher pair. Thus, detection of a binding or other reaction can include detection of an interaction between labels that are present on different components of the reaction.

In particular embodiments, a method set forth herein can be carried out under conditions wherein one or more of the nucleotides lack detectable labels. A method can be carried out under conditions wherein all of the nucleotides lack detectable labels. For example, the nucleotide(s) can lack an exogenous label. Exogenous labels include any labels that are not present in the structure of a natural nucleotide including, for example, an optical label such as a fluorophore, optical quencher, or chromophore.

In particular embodiments, a method set forth herein can be carried out under conditions wherein a nucleic acid, whether a template strand or its complement, lacks detectable labels. For example, a nucleic acid can lack an exogenous label, such as those set forth above.

In some embodiments, a method can be carried out under conditions wherein at least one nucleotide is undetectable including, for example, a condition wherein all of the nucleotides are undetectable. Alternatively or additionally, a method can be carried out under conditions wherein a nucleic acid, whether a template strand or its complement, is undetectable. A nucleotide or nucleic acid can be undetectable due to the use of a detection device or detection mode that is incapable of detecting signals produced by the nucleotides or nucleic acids. For example, an optical device can include an optical filter that rejects optical signals in a range produced by the nucleotides and/or nucleic acids. Alternatively or additionally, an optical device can be configured such that it does not substantially excite nucleotides and/or nucleic acids in a way that optically detectable signals are produced. As such the detection method of apparatus can be specific for a label on a polymerase.

A method set forth herein can be carried out in solution or on a solid support. A solution-phase method will be understood to be one where all components that participate in a reaction are in solution, the components including, for example, a nucleic acid, polymerase and nucleotide. A solid-phase reaction is one where one or more of the components occur in or on a solid support. For example, a nucleic acid, polymerase or nucleotide can be in or on a solid support during the course of a solid-phase reaction. A nucleic acid that is attached to the solid support can be a template nucleic acid such as one that is copied by a polymerase, a primer nucleic acid such as one that is extended by a polymerase, or a double stranded nucleic acid such as one that is acted upon by a polymerase.

Any of a variety of solid-support materials can be used in a method or composition set forth herein. Useful materials include, for example, those that are separable from each other such as beads, particles, microspheres, or chromatographic supports; and those that form a continuous material such as a flow cell, microchip or other chip, microscope slide or other planar surface, or the like. Particularly useful supports are those used for microarrays. Useful materials for a microarray or other solid support include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful substrates include those that allow optical detection, for example, by being translucent to energy of a desired detection wavelength and/or do not produce appreciable background fluorescence at a particular detection wavelength.

A reaction component can be attached to a solid support by methods known in the art. In some embodiments, a component such as a nucleic acid can be synthesized on a solid support by sequential addition of nucleotide units directly on the solid support. Methods known in the art for synthesis of a variety of nucleic acids on solid supports can be used including, for example, photolithographic techniques commercialized by Affymetrix (Santa Clara, Calif.) or Nimblegen (acquired by Roche, Basel Switzerland). Alternatively, components can be synthesized or otherwise obtained first, and then covalently attached to a solid support, for example, as used in array printing methods used by Agilent (Santa Clara, Calif.) and Oxford Gene Technologies (Oxford, UK) or BeadArray manufacture (Illumina, San Diego, Calif.). Nucleic acids can also be amplified on a surface using methods such as bridge amplification, rolling circle amplification or emulsion PCR as set forth in further detail elsewhere herein.

Reaction components can be attached to functional groups on a solid support. Functionalized solid supports can be produced by methods known in the art and, if desired, obtained from any of several commercial suppliers for beads and other supports having surface chemistries that facilitate the attachment of a desired functionality by a user. Exemplary surface chemistries that are useful include, but are not limited to, amino groups such as aliphatic and aromatic amines, carboxylic acids, aldehydes, amides, chloromethyl groups, hydrazide, hydroxyl groups, sulfonates or sulfates. If desired, a component can be attached to a solid support via a chemical linker. Such a linker can have characteristics that provide, for example, stable attachment, reversible attachment, sufficient flexibility to allow desired interaction with another reaction component, or to avoid undesirable binding reactions. Exemplary methods that can be used in the invention to attach polymer probes to a solid support are described in Pease et al., *Proc. Natl. Acad. Sci. USA* 91(11): 5022-5026 (1994); Khrapko et al., *Mol Biol (Mosk)* (USSR) 25:718-730 (1991); Stimpson et al., *Proc. Natl. Acad. Sci. USA* 92:6379-6383 (1995) or Guo et al., *Nucleic Acids Res.* 22:5456-5465 (1994), each of which is incorporated herein by reference in its entirety.

A reaction component can be attached to a support in a way that provides detection at a single molecule level or at an ensemble level. For example, a population of nucleic acids can be attached to a solid support in a way that labeled polymerases that interact with individual nucleic acid molecules in the population can be distinguished from labeled polymerases that interact with all other nucleic acid molecules on the support. Single molecule detection can also be achieved with a population of labeled polymerases that is attached to a solid support in a way that signals arising from a particular polymerase can be distinguished from signals arising from all other polymerases on the support. Reaction components can be separated from each other on a solid support due to surface features or contours such as those that form wells, posts, channels or the like. Alternatively or additionally, separation can be achieved by providing spacing between molecules that is greater than the resolution of a particular detection device that is in use.

Ensemble detection can be achieved for reaction components that are attached to a surface to form colonies or clusters for ensemble detection. Colonies of nucleic acids can be attached to a surface using methods known in the art such as bridge amplification or emulsion PCR. Useful bridge amplification methods are described, for example, in U.S. Pat. No. 5,641,658; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein by reference in its entirety. Another useful method for amplifying nucleic acids on a surface is rolling circle amplification (RCA), for example, as described in Lizardi et al., *Nat. Genet.* 19:225-232 (1998) and US 2007/0099208 A1, each of which is incorporated herein by reference in its entirety. RCA can also be used to amplify nucleic acids in solution to produce DNA concatamers that are subsequently attached to a surface or subsequently used as a template for producing surface attached copies, for example, as described in US 2008/0234136 A1 and U.S. Pat. No. 6,797,474, each of which is incorporated herein by reference in its entirety. Exemplary emulsion PCR methods are described in Dressman et al., *Proc. Natl. Acad. Sci. USA* 100:8817-8822 (2003), WO 05/010145, or U.S. Patent Publ. Nos. 2005/

0130173 or 2005/0064460, each of which is incorporated herein by reference in its entirety.

The complexity of an array can vary depending on the desired use of the array. Arrays useful in the invention can have complexity that ranges from about 2 different features to many millions, billions or higher. The density of an array can be from 2 to as many as a billion or more different features per square cm. For example an array can have at least about 100 features/cm$^2$, at least about 1,000 features/cm$^2$, at least about 10,000 features/cm$^2$, at least about 100,000 features/cm$^2$, at least about 10,000,000 features/cm$^2$, at least about 100,000,000 features/cm$^2$, at least about 1,000,000,000 features/cm$^2$, at least about 2,000,000,000 features/cm$^2$ or higher.

Detection can be carried out in a method set forth herein, using a technique that is appropriate to the label being used. In various embodiments, the technique will have a time resolution that can distinguish events occurring in the millisecond time range, for example, when used for pre-equilibrium kinetic analysis. Appropriate techniques include, but are not limited to, fluorescence, fluorescence (or Förster) resonance energy transfer (FRET), chemiluminescence, electroluminescence, Rayleigh Scattering, Mie Scattering, Raman scattering, electromagnetic energy absorption, electromagnetic energy polarization or electrical sensing (e.g. MOSFET, ISFET).

For light based approaches the detection system can include incident radiation and optical elements, e.g. filters, detectors, polarizers, lenses, to condition light that directly or indirectly propagates or to detect a signal from an optical label. In particular embodiments, the incident radiation in a light-based detection approach can be via total internal reflection fluorescence (TIRF), epi-illumination, surface plasmons, two-photon excitation, far field detection, polarized excitation and emission, or any form of electromagnetic radiation that is permuted when incident upon the sample, such that it can be detected.

Electrical sensing can be mediated via a label linked to a polymerase, nucleotide or other molecule to be detected. Examples include but are not limited to inorganic or organic molecules and nanoparticles. Using MOSFET technology, for example, as described in Bergveld, P., *Sensors and Actuators*, 88 (3), (2003) (which is incorporated herein by reference in its entirety), the measured signal can be the drain current which is dependent on the input voltage and the choice of linkage to the polymerase and/or nucleotide. Alternative schemes may be used in the ISFET format, such that a change in the electrical properties of a solution is detected.

A method of distinguishing nucleotide sequences, although exemplified herein with regard to a single nucleotide extension event, can be carried out for a number of different nucleotide species. For example, a method can include the steps of (a) providing a plurality of different nucleic acid molecules, wherein the different nucleic acid molecules are attached to a surface in the form of an array of nucleic acid features; (b) adding a plurality of polymerase-linked nucleotides to the nucleic acid features, (c) monitoring binding of the polymerase molecules to the nucleic acid features, thereby determining dwell time of the polymerase molecules at the nucleic acid features; and (d) identifying nucleic acid features of the array that correctly incorporate the nucleotide molecules based on the dwell time of the polymerase molecules at the nucleic acid features, thereby distinguishing the nucleotide sequences for the different nucleic acid molecules. The plurality of polymerase-linked nucleotides can be added to the array of nucleic acid features simultaneously, or sequentially. Because detection of binding events happens in real time and can distinguish discrete binding events, sequential binding event can be detected, even for stretches of homopolymer sequence. Thus, the binding and detection steps can be performed in a "one-pot" reaction, without the need to remove unincorporated nucleotides or modify the incorporated nucleotides.

Alternatively, nucleotides having reversible blocking moieties can be used, allowing for temporal control over the sequence and timing of incorporation events. Optionally, for embodiments that use nucleotides having reversible blocking moieties, the method can include removing or modifying the blocking moieties at the nucleic acid features that correctly incorporate the nucleotide molecules. Thus, the nucleic acid molecules at the features can be rendered extension competent for subsequent incorporation events. As one example, the method of the present disclosure can include sequential deliveries of different nucleotides. For example, the four different nucleotide species A, C, T and G can be delivered (in any order) to an array in four sequential steps. Furthermore, sequential delivery of different nucleotide species can constitute a cycle that is repeated multiple times. For example, the four steps whereby A, C, T and G are delivered to an array can be repeated in 2 cycles whereby the sum total of nucleotide delivery steps is A, C, T, G, A, C, T and G. The order of nucleotide additions is exemplary and can differ to suit a particular application of the methods. Furthermore, the order of nucleotide addition can be the same for one or more cycles of a sequencing reaction or the order can differ between cycles. The number of cycles can be at least 2, 3, 5, 10, 50, 100, 250, 500, 1000, 10000 or more. Typically, four different nucleotide species will be delivered per cycle, but if desired, fewer than four nucleotides can be delivered in a given cycle.

In a particular embodiment, one or more nucleotide species having blocking moieties can be delivered such that single base extension occurs. Deblocking and washing steps can be carried out between nucleotide addition steps. Typically a chemically reactive deblocking moiety is used; however a photo-sensitive block can be used for fast deblocking by light. Exemplary modifications that can be used to render a nucleotide reversibly blocked and respective deblocking reagents are described in U.S. Pat. Nos. 7,427,673; 7,414,116; 7,057,026; and 8,241,573 and PCT publications WO 91/06678 and WO 07/123744, each of which is incorporated herein by reference in its entirety. For embodiments where reversibly blocked nucleotides are used, the number of cycles can be at least 2, 3, 5, 10, 50, 100, 250, 500, 1000, 10000 or more thereby causing extension of a nucleic acid by at least 2, 3, 5, 10, 50, 100, 250, 500, 1000, 10000 or more nucleotides, respectively.

Example 1

Synthesis of PEG$_x$-6P-dA

Figure 5:
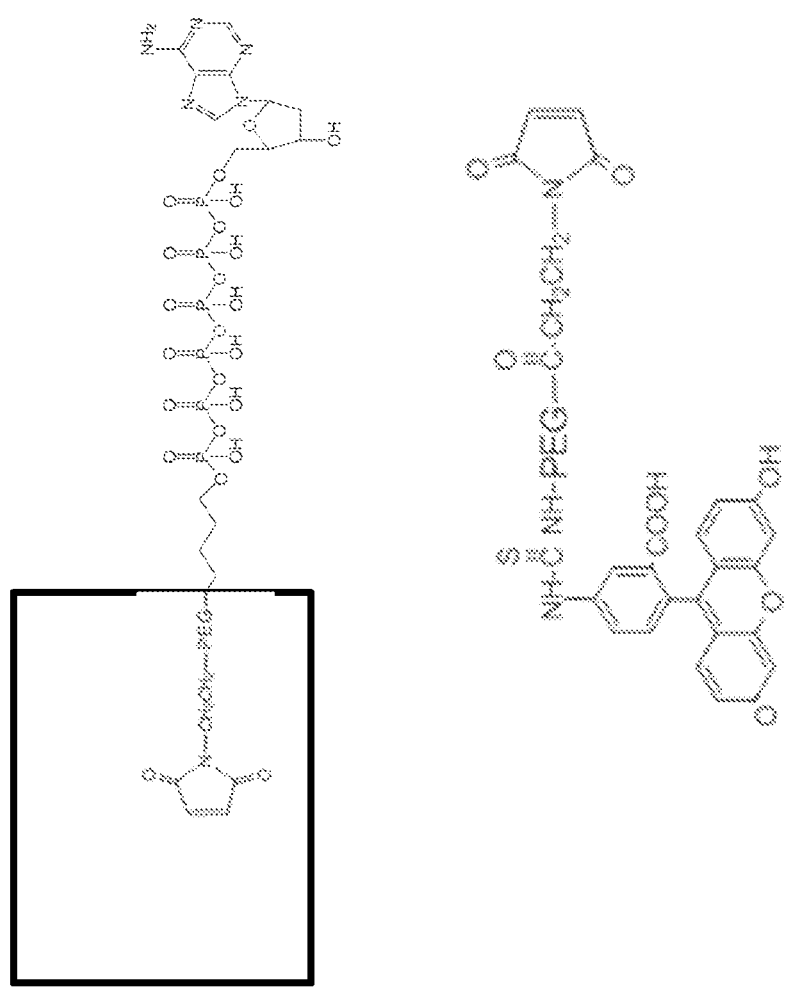
FIG. 5 shows the synthesized nucleotide analog according to one embodiment presented herein. Also shown is a dye-linker moiety as described herein.

Custom hexaphosphate nucleotide was purchased from MyChem (San Diego, Calif.). This compound contains a dATP molecule with three additional phosphate molecules that connect the nucleotide to a six carbon linker terminated with a amine functional group (FIG. 4). Maleimide-PEG$_x$-NHS ester (where x=2 or 12 PEG units) compounds were purchased commercially. NHS-ester/amine chemistry and subsequent purification was performed using manufacturers protocols. An example of a synthetic product is shown in FIG. 5.

Example 2

BSU Conjugation

Three different versions of the BSU polymerase were generated having a single point mutation to cysteine at one of three surface-exposed residues. The mutants generated were E341C, D575C and E406C.

Purified BSU Pol I containing a single cysteine point mutation was buffer exchanged into conjugation buffer (50 mM ACES pH 7.4, 20 mM NaCl, 0.2% Tween-20) using illustra NAP G-25 columns (GE). The protein was then concentrated to 100 uM and conjugated to either PEGx-6P-dA or PEG-Cy5 (FIG. 5) using a maleimide chemistry to form a covalent with the single point mutation cysteine on the surface of the protein. The protein contained no other cysteine residues. The labeling reaction was incubated at 22° C. for 1 hour, and followed two step purification to remove all excess maleimide compound. Labeling reactions were first purified using an affinity HisTrap spin column (GE) followed by two rounds of buffer exchange using an illustra NAP G-25 columns. Both purification methods followed standard manufacturer recommended protocols. The final storage buffer contained 50 mM ACES pH 7.4, 20 mM NaCl, 0.2% Tween-20, 1 mM DTT. Molar labeling efficiency was calculated spectrophotometrically for Cy5 labeled compounds using extinction coefficients of 170,000 $M^{-1}$ $cm^{-1}$ and 55,810$M^{-1}$ $cm^{-1}$ for Cy5 and BSU Pol I, respectively.

The ratio of enzyme to dye was titrated to determine optimal labeling efficiency. A ratio of [BSU]:[Dye] of 20× molar ratio was found to achieve labeling efficiencies of greater than 95%. Protein lots with labeling efficiencies of ≥95% were aliquoted and flash frozen in liquid $N_2$ and stored at −80° C. until use.

Each of E341C, D575C and E406C mutants were demonstrated to be efficiently labeled under the above described conditions for each of the following labels: Mal-Cy3, Mal-PEG-Cy5, Pal-PEG-FITC.

Example 3

Stopped Flow Incorporation of dCTP by BSU-PEG-Cy5

In order to test protein response to dCTP conditions under high ionic conditions, in the presence of covalently attached PEG-Cy5, a stopped flow incorporation assay was conducted using the conditions and protocols generally set forth in the incorporated materials of U.S. application Ser. No. 13/722,979, entitled APPARATUS AND METHODS FOR KINETIC ANALYSIS AND DETERMINATION OF NUCLEIC ACID SEQUENCES, filed on Dec. 20, 2012.

Figure 6:
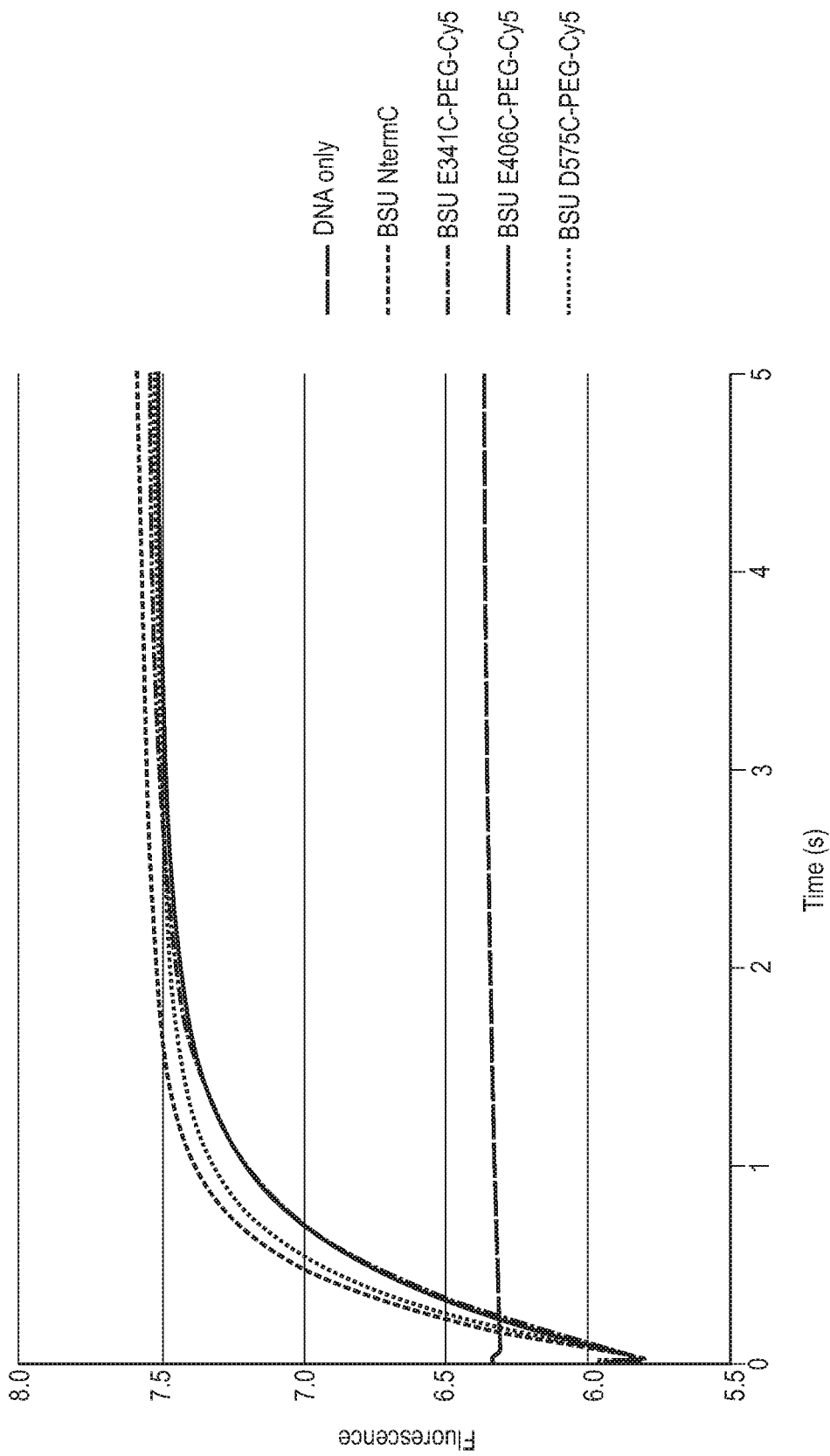
FIG. 6 shows the results of stopped flow assay to test incorporation of nucleotide using a dye-labeled polymerase.

The results are summarized in FIG. 6. The results indicated that only minor differences in $V_{off}$ and similar amplitude responses for each of the enzymes. The results show that PEG-Cy5 did not alter turnover under high salt conditions.

Example 4

Purification of Enzme-Nucleotide

The following protocol is used to remove free nucleotide-linker after reaction with the polymerase. Polymerase is labeled with 20-fold molar excess of nucleotide-linker compound. The mixture is then bound to a HisTrap Spin column and washed four times. Labeled polymerase is then eluted in high imidazole buffer followed by buffer exchange through a gel filtration column.

Example 5

Incorporation Assay

DNA titration experiments were performed using 200 nM (by Bradford) of enzyme labeled with dATP that was pre-incubated with varying concentrations of duplex DNA in reaction buffer (10 mM Tris pH 8.0, 50 mM NaCl, 1 mM DTT). Duplex DNA was constructed by annealing 1:1.1 molar ratios of primer (5'-Cy5-GCTTGCACAGGGCCTC-GAC-3') and template: (5'CGTTAGTAAGGTCGAGGC-CCTGTGCAAGC-3') oligonucleotides (IDT). The reaction was started by mixing in a final concentration of 10 mM $MgCl_2$ and stopped at various time points by addition of 500 mM EDTA.

Misincorporation studies were performed as previously described; however, the correct templating base was replaced with a base to form a dATP:dA mismatch at the incorporation site. Both templates were then chased with correct nucleotide (either dATP or dTTP).

Evaluation of different cysteine labeling positions was performed by purifying three different BSU mutants with cysteine point mutations at either E341, E406, or D575. These positions were selected using the criteria of conservation, surface accessibility, and proximity to the active site. The enzymes were labeled with either $PEG_2$-dATP or $PEG_{12}$-dATP. Incorporation of the enzyme linked nucleotides was performed by pre-incubating 200 nM enzyme with 1000 nM DNA (as previously described). The reaction was then initiated by addition of 10 mM $MgCl_2$ and quenched at various times by addition of EDTA. The control assay contained unlabeled BSU to confirm that no free nucleotide remained after the labeling and purification.

Figure 7:
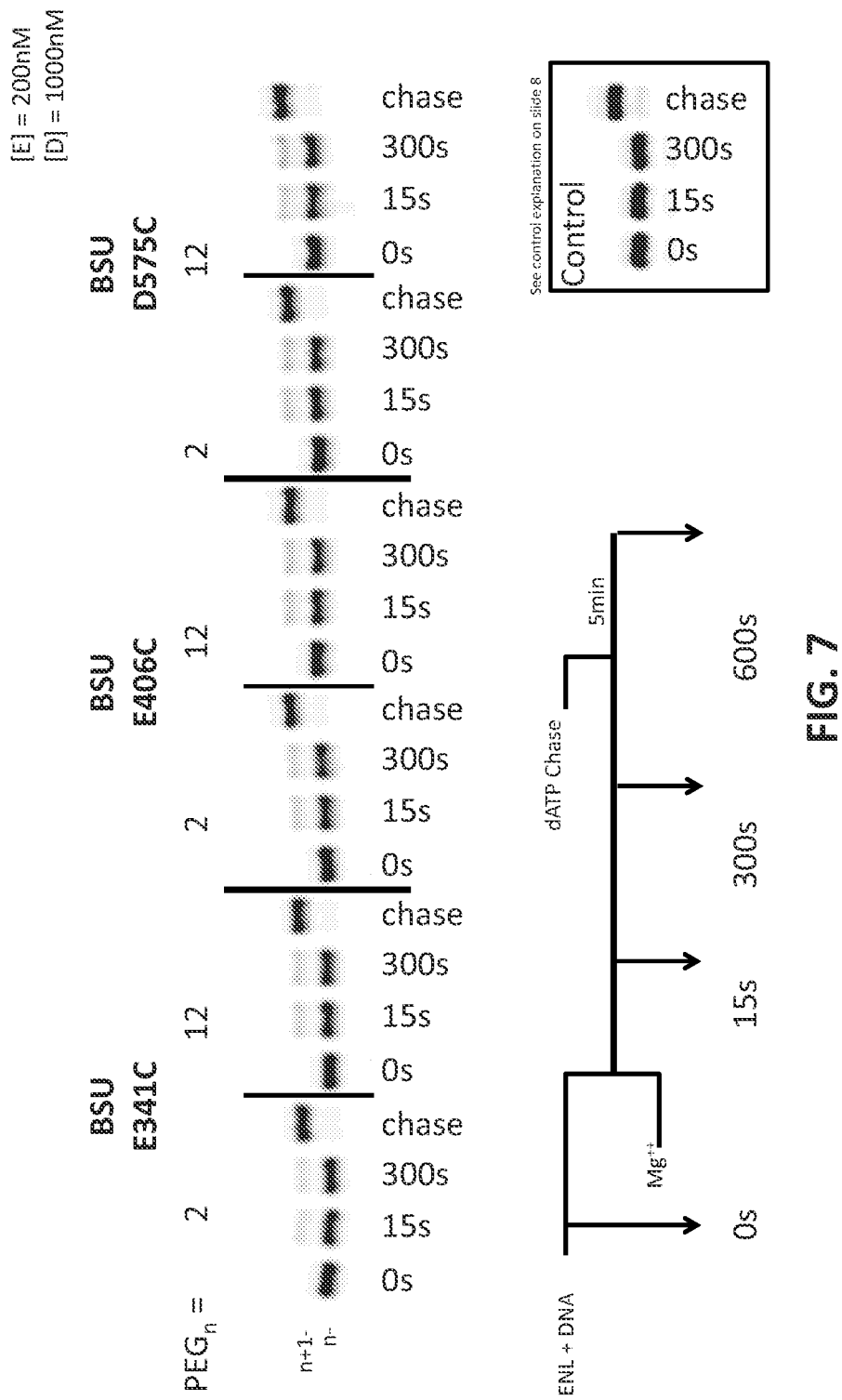
FIG. 7 sets forth typical result of an incorporation study.
Figure 8:
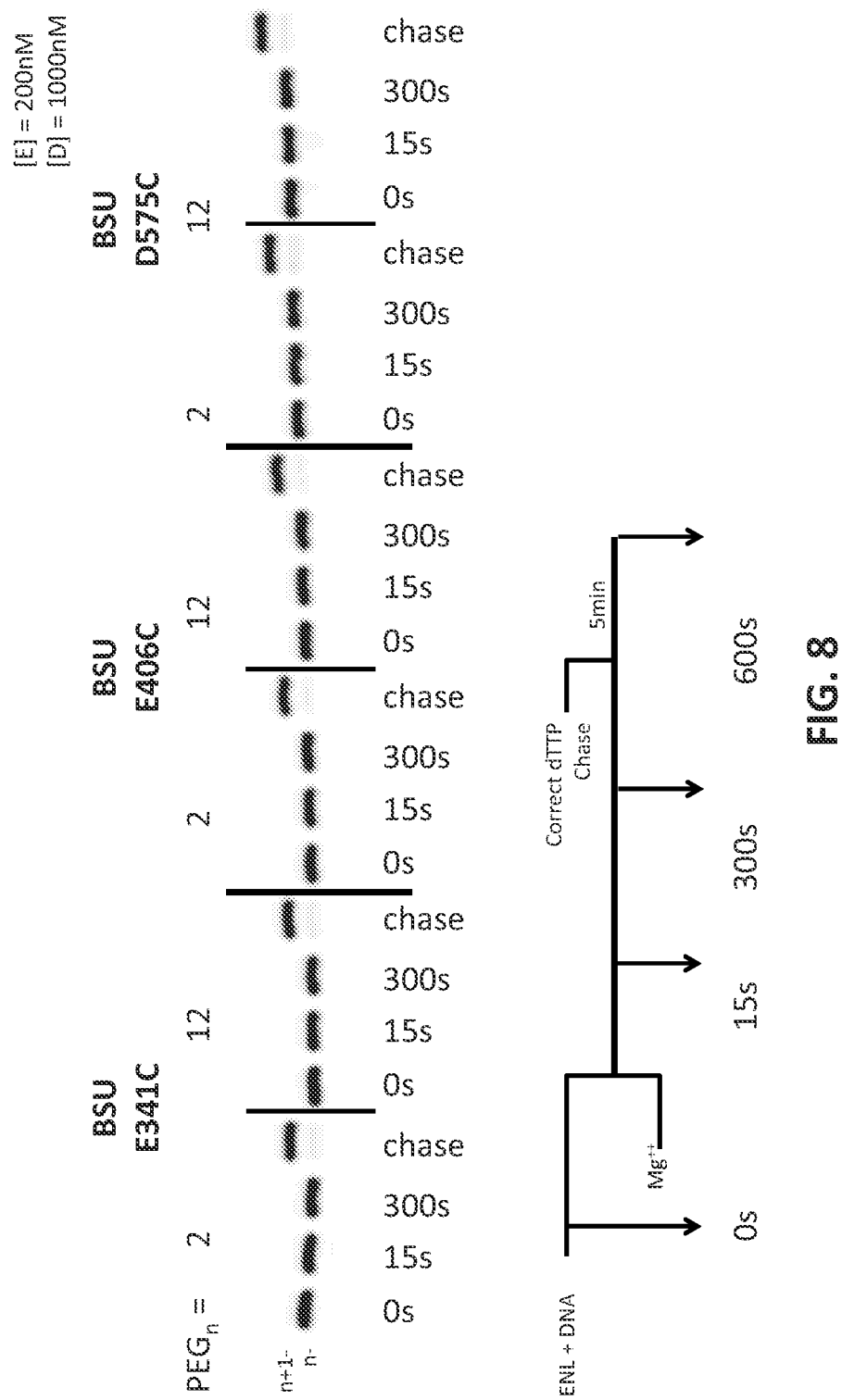
FIG. 8 sets forth typical result of a misincorporation study.
Figure 9A:
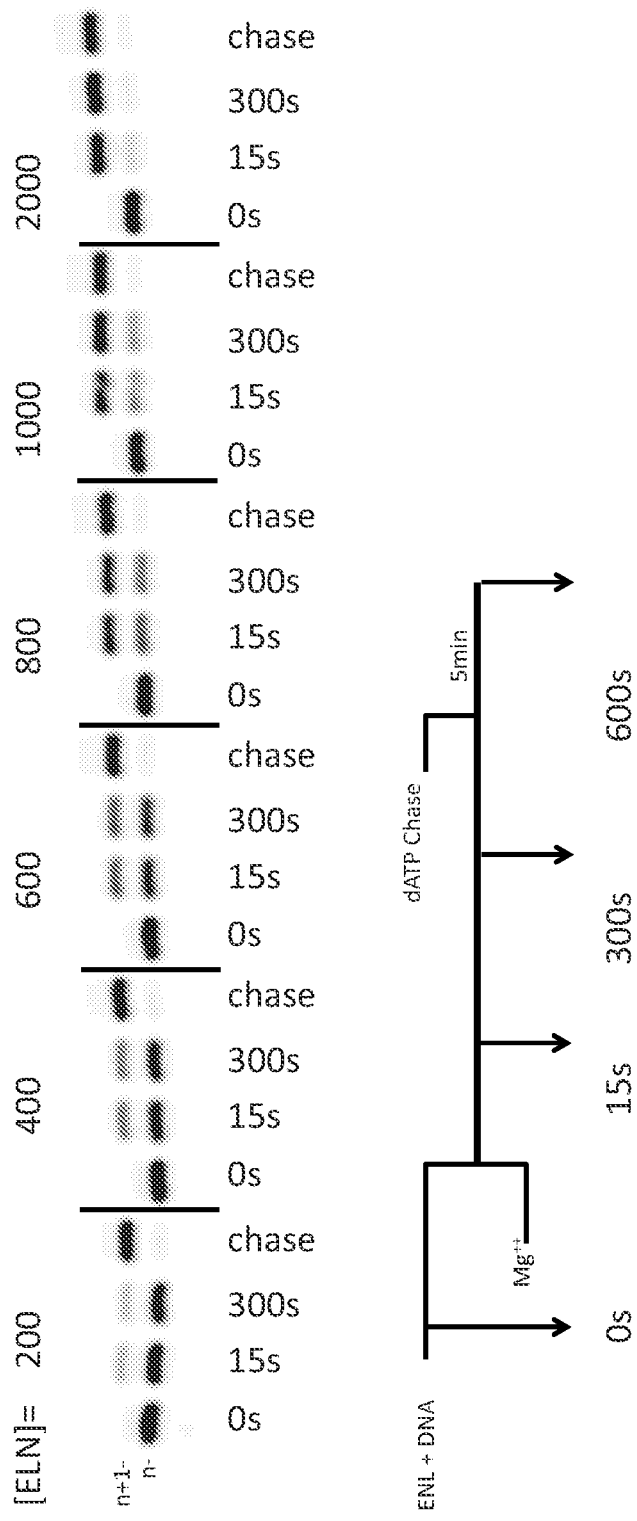
FIGS. 9A-C sets forth results of an incorporation study to show concentration dependence of product formation.
Figure 9B:
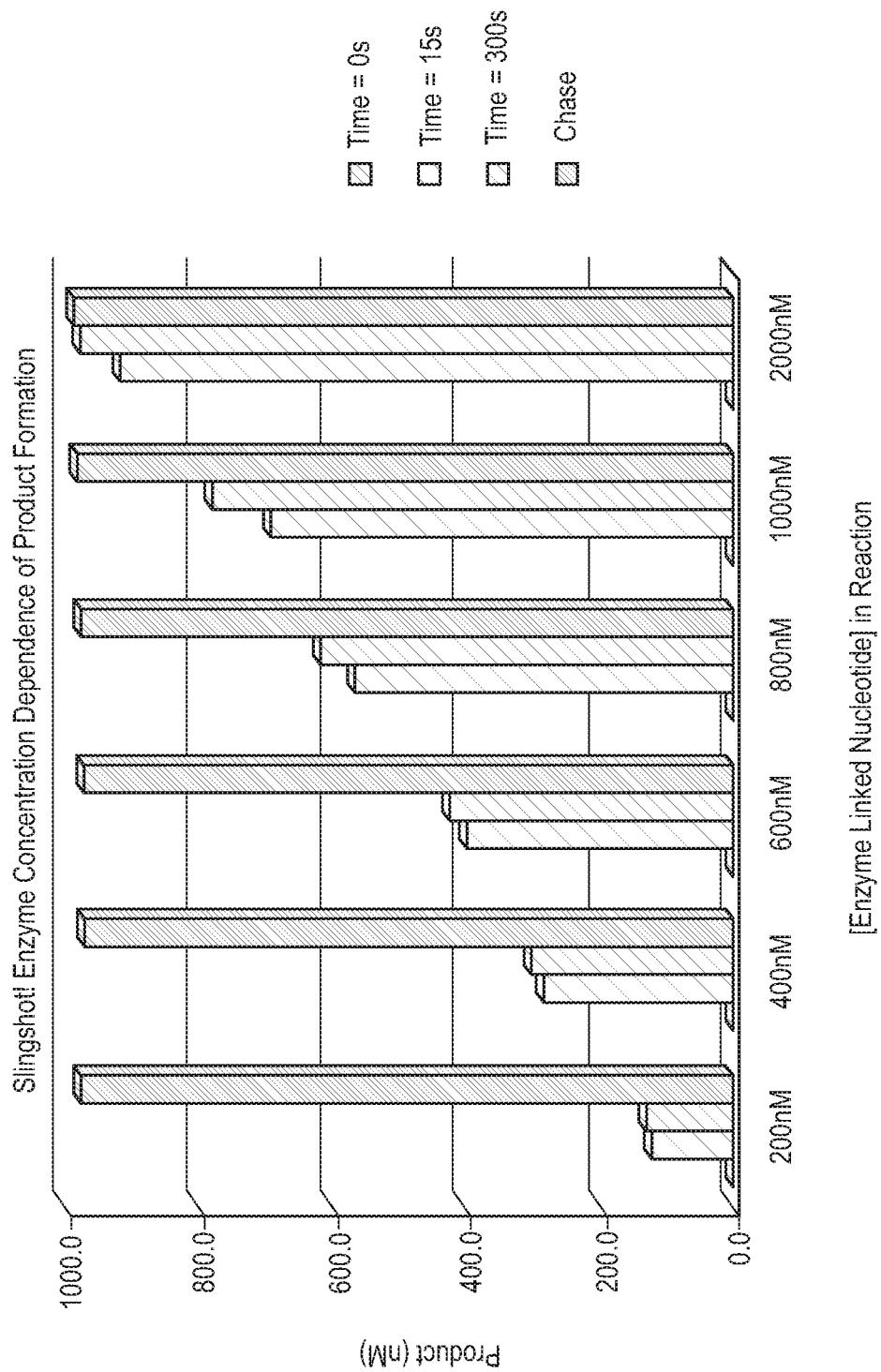
Figure 9C:
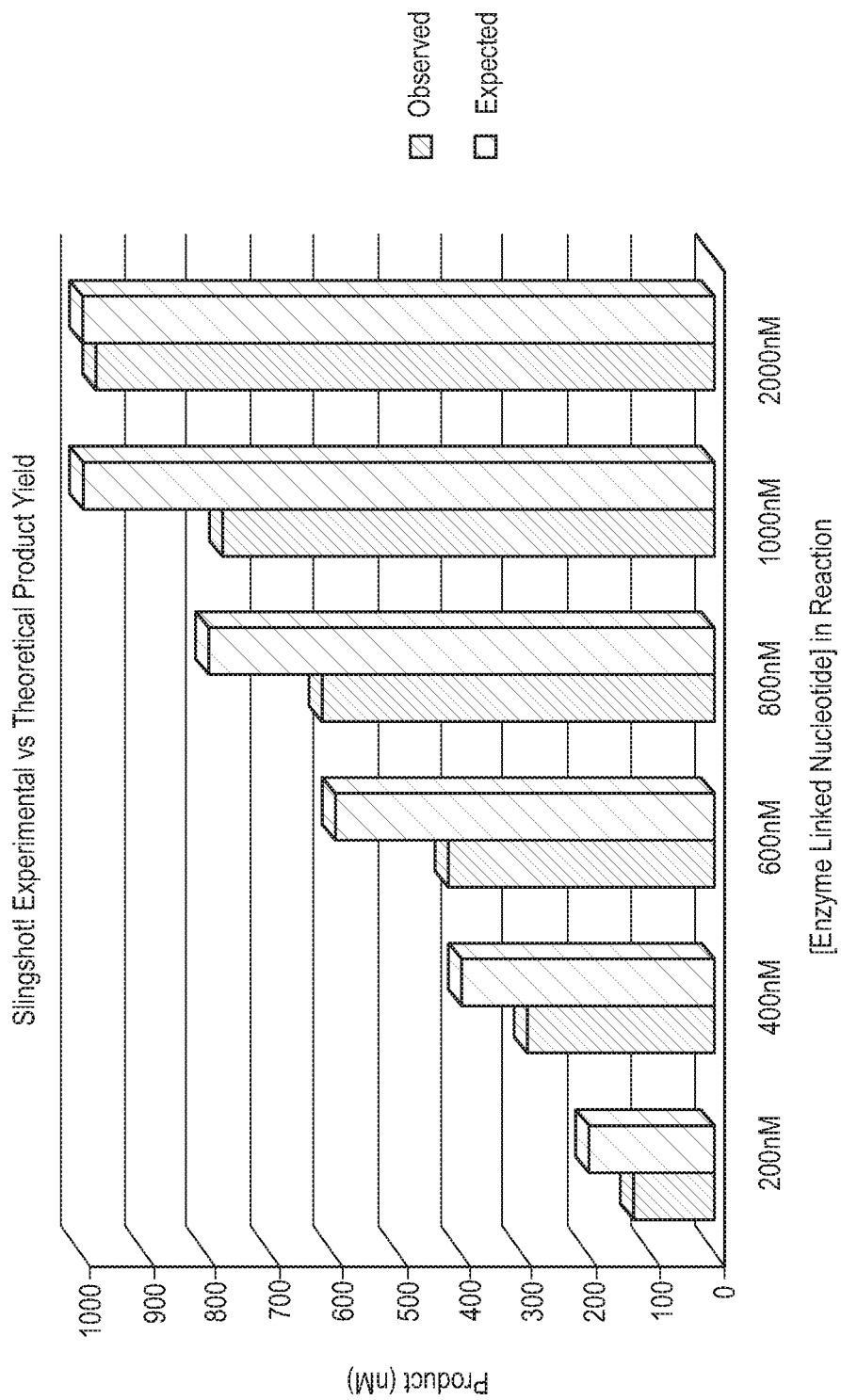

Representative results of the incorporation assay are set forth in FIG. 7. Representative results of the misincorporation assay are set forth in FIG. 8. Representative results showing concentration dependence on product formation are set forth in FIG. 9.

These studies confirm that nucleotides can be covalently linked to a polymerase and the polymerase can still retain catalytic activity. Catalytic activity is fast, with a reaction completion time well under 15 s. Product formation (n+1) is proportional to the amount of enzyme linked nucleotide in the reaction.

These results further confirm that enzyme linked nucleotides maintain natural polymerase discrimination against incorrect base pairing. Specifically, no product was observed when non-Watson-Crick base pairing was probed.

These results further confirm that free nucleotide can be successfully removed after labeling with a 20 fold molar excess, thereby removing contamination that would prevent detection of nucleotide incorporation during sequencing reactions.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A modified DNA polymerase comprising:
  a) a point mutation wherein a surface-exposed amino acid residue is replaced with a cysteine residue;
  b) a flexible linker having a first end and second end, the first end covalently attached to the cysteine residue;
  c) a nucleotide attached to the second end of the flexible linker, wherein the flexible linker attachment to the nucleotide allows, the nucleotide to interact at a catalytically active region of said modified DNA polymerase and incorporate the nucleotide to the 3' end of a polynucleotide in the presence of a template nucleic acid sequence thereby producing a detectable increase in dwell time at the site of incorporation; and
  c) an optically detectable label comprising a fluorophore attached to the modified DNA polymerase.

2. The modified DNA polymerase of claim 1, wherein the linker attachment to the nucleotide occurs at the 5' gamma phosphate of the nucleotide.

3. The modified DNA polymerase of claim 1, wherein said nucleotide comprise one of the group of nucleotides consisting of: dCTP, dATP, dGTP, dTTP, and dUTP.

4. The modified DNA polymerase of claim 1, wherein said nucleotide comprises polymeric phosphate comprising 3, 4, 5, 6 or greater than 6 phosphates.

5. The modified DNA polymerase of claim 4, wherein said polymeric phosphate comprises hexaphosphate.

6. The modified DNA polymerase of claim 1, wherein said flexible linker is of a length so as to create a relative concentration of said nucleotide in solution of greater than 1 µM, 10 µM, 100 µM, or greater than 1 mM.

7. The modified DNA polymerase of claim 1, said flexible linker having a length of greater than 50, 60, 70, 80, 90, 100, 110, 120, 130, 140, 150, 160, 170, 180, 190 or greater than 200 Angstrom.

8. The modified DNA polymerase of claim 1, said flexible linker having a length of less than 200, 190, 180, 170, 160, 150, 140, 130, 120, 110, 100, 90, 80, 70, 60 or less than 50 Angstrom.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 1
gcttgcacag ggcctcgac                                            19

<210> SEQ ID NO 2
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 2
cgttagtaag gtcgaggccc tgtgcaagc                                 29